(12) United States Patent
Wassermann et al.

(10) Patent No.: US 7,217,237 B2
(45) Date of Patent: May 15, 2007

(54) CLOSING SYSTEM AND ELECTRONIC CONTROL METHOD

(75) Inventors: Helmut Wassermann, Struwelpeterstrasse 5B, München (DE) D-81739; Sebastian Schostek, München (DE); Chi-Nghia Ho, München (DE)

(73) Assignees: Dieter Jocham (DE); Helmut Wassermann (DE)

( * ) Notice: Subject to any disclaimer, the term of this patent is extended or adjusted under 35 U.S.C. 154(b) by 0 days.

(21) Appl. No.: 10/496,423

(22) PCT Filed: Nov. 19, 2002

(86) PCT No.: PCT/EP02/12963

§ 371 (c)(1),
(2), (4) Date: Apr. 18, 2005

(87) PCT Pub. No.: WO03/043534

PCT Pub. Date: May 30, 2003

(65) Prior Publication Data

US 2005/0240144 A1 Oct. 27, 2005

(30) Foreign Application Priority Data

Nov. 20, 2001 (DE) ................................ 101 56 558
Aug. 27, 2002 (DE) ................................ 102 39 309

(51) Int. Cl.
*A61F 2/00* (2006.01)
(52) U.S. Cl. ....................................................... 600/29
(58) Field of Classification Search ............ 600/29–32; 128/DIG. 25
See application file for complete search history.

(56) References Cited

U.S. PATENT DOCUMENTS 4,417,567 A    11/1983 Trick
(Continued)

FOREIGN PATENT DOCUMENTS

DE        35 39 498 A1    5/1987
(Continued)

OTHER PUBLICATIONS

Kandler et al., "CMOS Compatible Capacitive Pressure Sensor with Read-Out Electronics", International Conference on Micro Electro, Opto, Mehanical Systems and Components, Micro System Technologies, pp. 574-580, 1990.

(Continued)

*Primary Examiner*—John P. Lacyk
(74) *Attorney, Agent, or Firm*—Lerner, David, Littenberg, Krumholz & Mentlik, LLP

(57) ABSTRACT

A closing system is described and a correspondingly suitable method for the selective opening and closing of a tubular body organ, comprising a closing element and a regulating system controlling the closing element. Furthermore described are a method and a system for the electronic control of an artificial fine-sensory sphincter implant, with at least one sensor signal or, respectively, sensor value acting—in the method or, respectively, in the system—analog to the difference between the internal bladder pressure and the cuff pressure, and being converted in an analog or digital electronic circuit by means of calculator and comparator functions or, respectively, calculator and comparator elements and being compared with reference values such that an actuator system will be controlled such that the cuff pressure or, respectively, the differential pressure between cuff and urinary bladder moves either in a low area limited by two threshold values or above a specific safety pressure or below that in case of miction.

30 Claims, 14 Drawing Sheets

U.S. PATENT DOCUMENTS

Figure 1A:
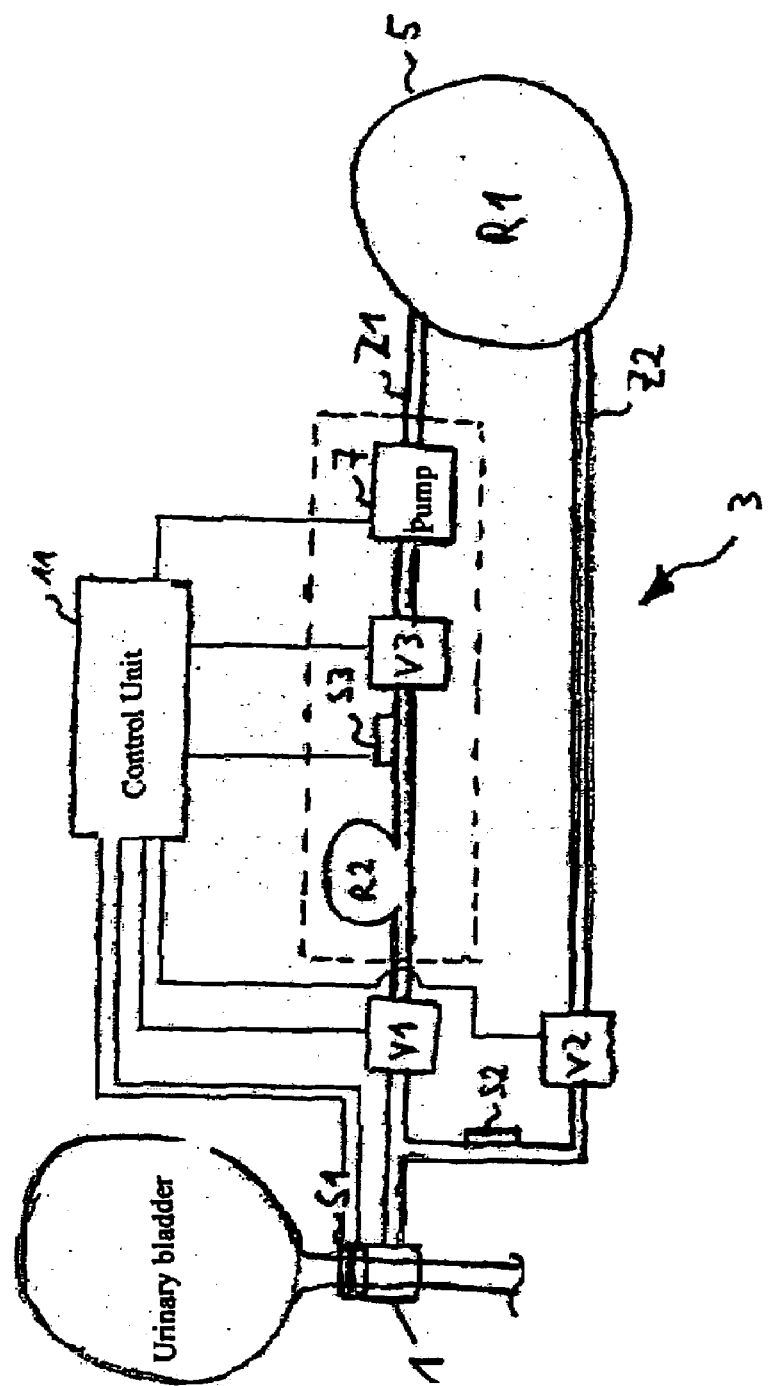

| | | |
|---|---|---|
| 4,571,749 A | 2/1986 | Fischell |
| 4,682,583 A * | 7/1987 | Burton et al. .................. 600/31 |
| 4,721,509 A | 1/1988 | Craggs |
| 4,994,020 A | 2/1991 | Polyak |
| 5,078,676 A | 1/1992 | Baily |
| 6,074,341 A | 6/2000 | Anderson et al. |
| 6,095,969 A * | 8/2000 | Karram et al. ................. 600/31 |
| 6,135,945 A | 10/2000 | Sultan |

FOREIGN PATENT DOCUMENTS

| | | |
|---|---|---|
| DE | 90 10 783.7 U1 | 10/1990 |
| DE | 690 02 920 T2 | 5/1991 |
| DE | 41 40 055 A1 | 6/1992 |
| DE | 43 31 658 A1 | 3/1995 |
| DE | 198 45 292 A1 | 5/1999 |
| DE | 100 13 519 A1 | 10/2001 |
| EP | 0 202 815 A2 | 11/1986 |
| EP | 0 314 258 A2 | 5/1989 |
| EP | 0 409 592 B1 | 1/1991 |
| WO | WO-98/31301 A1 | 7/1998 |
| WO | WO-00/15140 A1 | 3/2000 |
| WO | WO-01/45487 A2 | 6/2001 |
| WO | WO-01/50833 A2 | 7/2001 |

OTHER PUBLICATIONS

Dudaicevs, "A Fully Integrated Surface Micromachined Pressure Sensor With Low Temperature Dependence", Transducers, pp. 616-619, 1995.

Lerch et al., "A Programmable Mixed-Signal ASIC For Data-Acquisition System In Medical Implants", International Solid-State Circuits Conference, pp. 160-161, 1995.

Atala et al., Inplantation In Vivo And Retrieval Of Artificial Structures Consisting Of Rabbit And Human Urothelium And Human Bladder Muscle, J. Urol, vol. 150, pp. 608-612, 1993.

Jocham et al., "Praxis der Urologie II", Stuttgart: George Thieme, 1994/2002.

Wassermann, "Kunstliches harnableitendes System", Medizintechnik in Bayern, vol. 2, 2002.

Wassermann, "Artificial Urinary Diversion System", Bavarian Medical Technologies, vol. 2, 2002.

* cited by examiner

Method for regulation of the urethra closing pressure with admission pressure reservoir

CLOSING SYSTEM AND ELECTRONIC CONTROL METHOD

The following invention relates to a closing system and a correspondingly suitable method for the selective opening and closing of a tubular body organ.

From DE 43 31 658, an implantable device for the selective opening and closing of tubular body organs is known, with an elongated valve body being provided which is insertable into the tubular body organ. The valve body has a shutoff device which can be selectively closed and released. To this end, the valve body has an elastic hose section in which an inflatable body is arranged which is inflatable by a fluid and then closes the lumen of the hose section. Opening as well as closing is done by manual handling, i.e. inflation of the inflatable body is done by manual operation of a pump and opening is by manual operation of a switch. In principle, however, it must be taken care, with the known system, that the inflatable body will not be inflated so much that, on the one hand, the bodily organ will also enlarge and expand as a result of the frequent opening and closing, and on the other hand, the pressure generated by the inflatable body would cut the blood circulation of the body organ so that the tissue of the body organ would necrotize. Thus, these specifications require that closing the body organ with the known system is only possible within a limited pressure range; however, developing pressure peaks or, respectively, short-term pressure loads or, respectively, pressure increases in the body organ cannot ensure a secure closing of the body organ since the known system is not suitable for short-term following.

Accordingly, one objective of the present invention is to further develop the known closing system or, respectively, the known method for the selective opening and closing of a tubular body organ such that any pressure increases in the body organ to be closed will be counteracted short-term and the risk of necrosis will be nearly excluded.

Another objective of the present invention is to provide a closing system which ensures continence at any time.

These objectives are solved by the technical device with the characteristics of Claim 1 and by the technical method with the characteristics of Claim 9.

In accordance with the application, the closing system or, respectively, the method according to the invention for the selective opening and closing of a tubular body organ provides a closing element and a regulating system controlling the closing element, with the regulating system setting a first condition of the closing system and returning, in a self-regulating manner, a deviation from the first condition back to the first condition. This measure in accordance with the application will achieve that—with pressure peaks or, respectively, pressure loads occurring due to coughing, sneezing, laughing or bending over—the required objectives of the closing system can still be met. For example, if the closing system is applied at the urethra, this measure in accordance with the application can provide a sphincter replacement system which replaces the function of the outer sphincter of the urethra in adult humans. Thus, the closing system in accordance with the application can be used as an implantable adaptive fine-sensory sphincter replacement system. Due to the fact that a first condition of the regulating system will be left only for a short time because of pressure peaks, the risk of necrosis can be reduced and, respectively, necrotic phenomena can be prevented. With the closing system in accordance with the application will thus be prevented that a constantly high closing pressure acts upon the body organ or, respectively, the urethra which would cause the surrounding body organ tissue to develop necrosis or inflammations, respectively. Since the closing system in accordance with the application provides a simply conceived self-regulation, implantation into the human body is also safe. Moreover, it is possible to manually control miction via this easy-to-operate closing system, with the control of the closing system also being possible automatically by tapping the neurological signals directly on the body organ's nerve path in case of the urethra of the ureteral sphincter, by means of an artificial synapse. With the closing system in accordance with the application, it is moreover possible that the energy consumption is kept low due to the simplicity of the closing system, thus providing a long service life. With the closing system in accordance with the application, the patient will regain a large measure of life quality by ensuring his or her continence with this implant and will not be limited in his or her radius of action since the system is maintenance-free.

Additional advantageous embodiments of this invention are the subject of subclaims.

If the regulating system with the closing element in accordance with claim 2 is designed as a closed circuit, a separate supply of transmission medium will not be required, for example hydraulic agents.

With the characteristics presented in claim 3, the self-regulating closing system will be converted in a simple manner so that the closing system as such is easy to implant and has only low energy consumption. Self-regulation will particularly be achieved by the alternate opening and closing of the shutoff valves. At this point, however, reference should be made here that a quick-action pump or, respectively, a quick-action actuator may be used instead of the pump device and a first shutoff valve.

To be able to best possibly adjust self-regulation depending on the body organ, i.e. keeping the closing pressure at a specific threshold value and setting a corresponding working pressure in this respect, different sensor elements are provided which, in suitable positioning, will optimally bring about the self-regulating measure.

Additional advantageous embodiments are the subject of the remaining subclaims.

On the basis of the following drawing, a preferred embodiment of the subject of the application will be described.

FIG. 1A shows the closing system which, in this case, selectively opens and closes a urethra as the body organ. With the closing system in accordance with the application, the urethra has a closing element 1 which is hydraulically controllable in this embodiment. Incidentally, it is pointed out that any other control is also conceivable. A regulating system 3—in this case hydraulic—is connectable to the closing element 1. The regulating system 3 serves to adjust a first condition of the closing system, for example a closing condition of the closing element 1. For this, the regulating system 3 in its hydraulic design has a first reservoir 5 to build up, via a pump device 7, a specific pressure, a so-called closing pressure on the closing element 1. The connecting line arriving at the closing element divides into a first feed line Z1 and a second feed line Z2, with the first feed line having the pump device 7 and advantageously a first shutoff valve V1, and the second feed line having a second shutoff valve V2, with the first feed line as well as the second feed line being connected with the first reservoir 5. Conventionally, the closing system according to the application can also merely be used as a device for the selective opening and closing of a body organ, in this case the urethra. To operate the selective opening and closing, it is advantageous that the pump device 7, the first shutoff valve V1 and the second shutoff valve V2 are connected with a control unit 11 which takes over the conventional opening and closing of the closing element 1. The closing system according to the application furthermore has a first sensor unit S1, which is provided on the closing element 1 preferably upstream of the tubular body organ, also a second sensor unit S2 which measures the pressure in the connection line and a third sensor unit S3 on the pump device 7. This enables a differential pressure measurement.

The closing system according to the application now works according to the following functional principle.

The pump device 7 avails itself from the reservoir 5 as the feed supply and produces a closing pressure on the closing element 1 which is selected such that the closing pressure seals the body organ via the closing element, however, does not impair the blood circulation in the body organ. The closing pressure is equivalent to a pressure range which depends on various parameters, such as e.g. body organ, vessel gauge, blood circulation intensity, etc.

In case of a short-term pressure increase in the body organ, for example with the urethra in the urinary bladder, due to coughing, sneezing, laughing or other exertion, the closing pressure is not sufficient and there would be a short-term flow-through in the body organ. In this case, it is of advantage if the closing pressure will also increase short-term to thus further maintain the seal of the body organ. The short-term increase of the closing pressure caused in the closing system according to the application will, however, not lead to any necrosis formation, i.e. the blood circulation in the body organ will be affected for only a short time and will thus not be damaging for the body organ. To maintain this mechanism, it is necessary that the regulating system 3 has different pressure ranges. In the embodiment presented in FIG. 1A, the pump device 7 which is, for example, designed as a quick-action pump or even as a fast actuator will generate the required closing pressure via the first shutoff valve V1. To this end, the second shutoff valve V2 must be closed. When reaching the closing pressure, the first shutoff valve V1 is closed, with the pump device 7 building up to the first shutoff valve V1 a working pressure which is increased versus the closing pressure. Should flow-through be effected through the body organ with the closing element, merely the second shutoff valve V2 must be opened to reduce the closing pressure via reservoir 5. If there are, however, upstream of the closing element 1 pressure peaks or, respectively, short-term sustained pressure loads, they will be registered or, respectively, recorded with the sensor device S1 and transmitted to the control unit 11. The control unit 11 opens nearly simultaneously the first shutoff valve V1 so that the increased working pressure is applied to the closing element 1 and thus ensures, short-term, that the body organ is also sealed versus pressure peaks. It is here conceivable that, depending on the circulation function of the body organ, the control unit 11, after a time constant, will close the first shutoff valve again and opens the second shutoff valve to regulate the increased working pressure down to the required closing pressure. Simultaneously or intermediately, the pump device 7 can again build up an increased working pressure which is applied to the first working valve V1 and thus preparing itself for a second action.

Thus, the regulating system 3 according to the application is able, in this manner, to return from a first condition of the closing system—which can conventionally be compared with the closing of the body organ via the closing element 1 via the selective opening—any deviation of the first condition back to the first condition in a self-regulating manner. This measure achieves that the closing system will meet the task of the closing system in any situation, thus also in case of strains, such as coughing or sneezing. Since the closing pressure is adjusted, by means of a fine sensory control, to the pressure prevailing upstream in the body organ or, respectively, the bladder pressure in the urinary bladder, necrotic manifestations will be prevented which will normally be caused by a constantly high closing pressure which suppresses the blood circulation in the body organ and thus causes long-term damage.

At this point, it should once again be emphasized that—as shown in FIG. 1A—the pump device 7 can also be replaced via a normal pump in combination with a second reservoir R2 and a third shutoff valve V3. In this case, the working pressure which is increased versus the closing pressure will be reached due to the fact that the pump—with opened third shutoff valve—applies pressure to reservoir R2 up to the required working pressure, after which the third shutoff valve V3 will then be closed. This measure will achieve that the use of a quick-action pump will not be required since the short-term application of pressure on the closing element 1—upon occurrence of pressure peaks in excess of the working pressure built up in the second reservoir R2—is applied to the closing element by opening the first shutoff valve.

Basically, it should be made clear that the sensor elements are not merely considered as pressure sensors, but that the pressure can also be determined with capacitive or inductive sensors, with volume changes also able to be measured via ultrasound or via foil strain gauges, or a change in distance resulting with a pressure increase being measured by light.

According to another aspect, this invention relates to a method for the electronic control of an artificial fine-sensory sphincter implant, especially to avoid strain incontinence and necrosis on the urethra, and a system for the electronic control of an artificial fine-sensory sphincter implant. Through this invention, the hitherto existing system of an artificial sphincter implant, expanded by a fine sensory system and an actuator system, is to be controlled such that not only complete continence can be ensured but also, at the same time, minimizing the risk of necrosis generated due to pressure which is excessive and applied for too long to the natural urethra.

Prerequisite for this is an intelligent, electronic control which recognizes different strain situations and—by increasing the cuff pressure—will prevent incontinence in case of dynamic strain, such as coughing or laughing for example, and at the same time, at rest conditions, will ensure sufficient blood circulation of the urethra tissue through corresponding pressure reductions. Since this electronic circuitry will be used in a medical implant, it must meet certain requirements such as reliability over long periods of time, minimum power consumption, small physical dimensions and individual adaptability.

The additional objective of the invention will follow directly from this.

Thus, in accordance with the invention, a method for the electronic control of an artificial fine-sensory sphincter implant will furthermore be provided, as it is defined in claim 12.

In accordance with the invention, a system for the electronic control of an artificial fine-sensory sphincter implant will furthermore be provided, as it is defined in claim 25.

Additional advantageous and/or preferable embodiments of the invention are the subject matter of the subclaims.

In the following, this aspect of the invention will be described in more detail merely by way of example and without limitation, and with reference to the Figures as well as to advantageous and/or preferred embodiments.

The meaning of the references used is provided in the list below. The terms of signal and value are here used synonymously.

(1) Differential pressure signal, bladder/cuff pressure difference
(2) Monostable threshold signal, safety threshold
(3) Bistable threshold signal, normal pressure threshold
(4) Cuff pressure
(5) Monostable reference signal, zero integration offset
(6) Monostable threshold signal, integration threshold
(7) Admission pressure signal
(8) Monostable threshold signal, admission pressure threshold
(9) Dynamic strain
(10) Monostable threshold signal, pressure compensation threshold
(11) Internal bladder pressure
(12) Output signal or, respectively, output value of the adding function, lower threshold value
(13) Output signal or, respectively, output value of the integrator function
(14) Output signal or, respectively, output value of the differentiator function
(15) Increase of cuff pressure
(16) Decrease of cuff pressure
(17) Admission pressure
(18) Increase of admission pressure
(19) Output signal of the integrator function of the delay block
(20) Dynamic strain
(21) Area of retrogressive integration
(22) Area of progressive integration
(23) Method for regulating the urethra closing pressure by means of an inflatable cuff, a fluid reservoir, a pump, and a valve via hydraulic connections
(24) Hydraulic connection
(25) Cuff
(26) Controllable valve
(27) Bi-directional pump
(28) Fluid reservoir
(29) Admission pressure reservoir
(30) Method for regulating the urethra closing pressure by means of an inflatable cuff, a fluid reservoir, a pump, three valves and an admission pressure reservoir via hydraulic connections
(31) Urethra closing pressure
(32) Differentiator function
(33) Adding function
(34) Integrator function
(35) Parameter variation
(36) Comparator element
(37) Integrator function of the delay block

THE FIGURES SHOW

FIG. 1A: shows a closing system which selectively opens and closes a body organ.

Figure 1B:
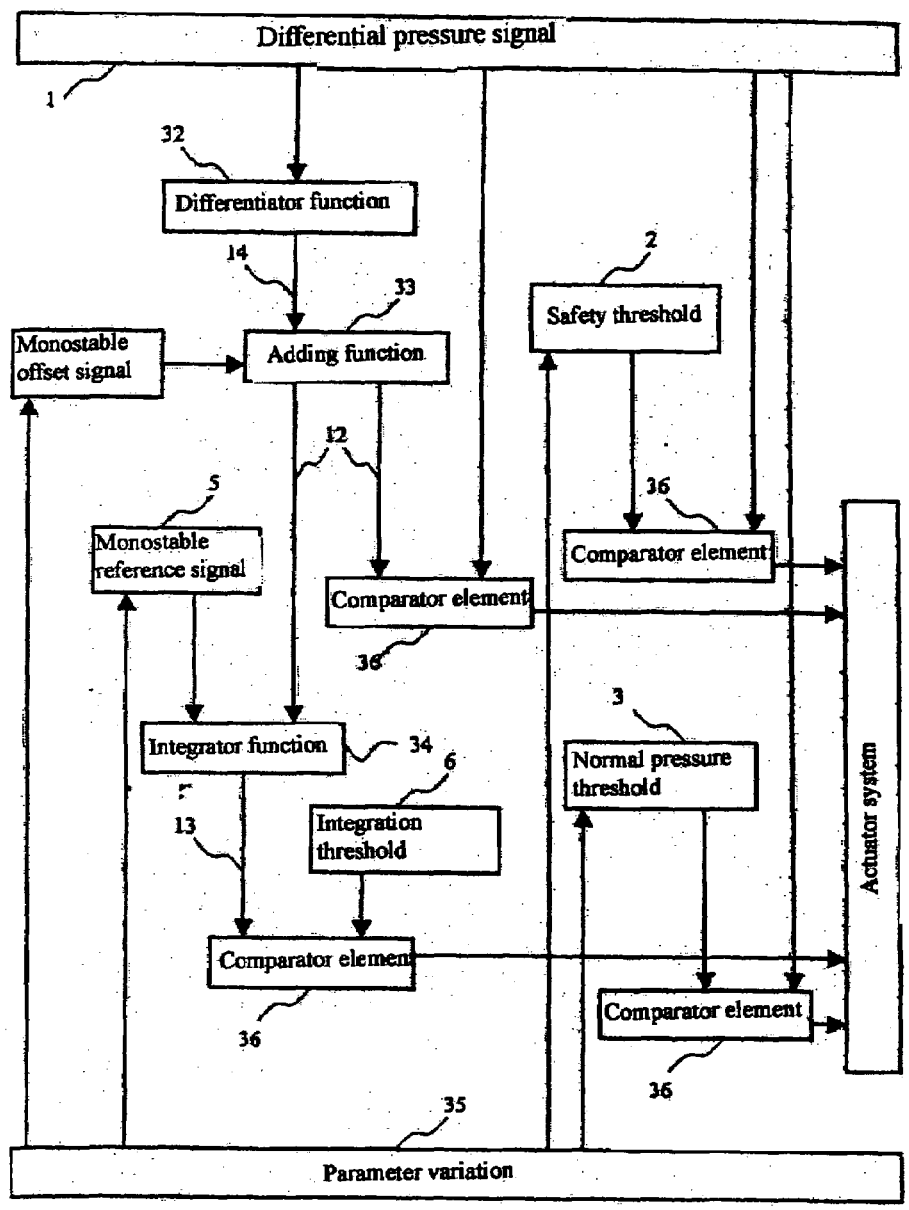
Figure 2:
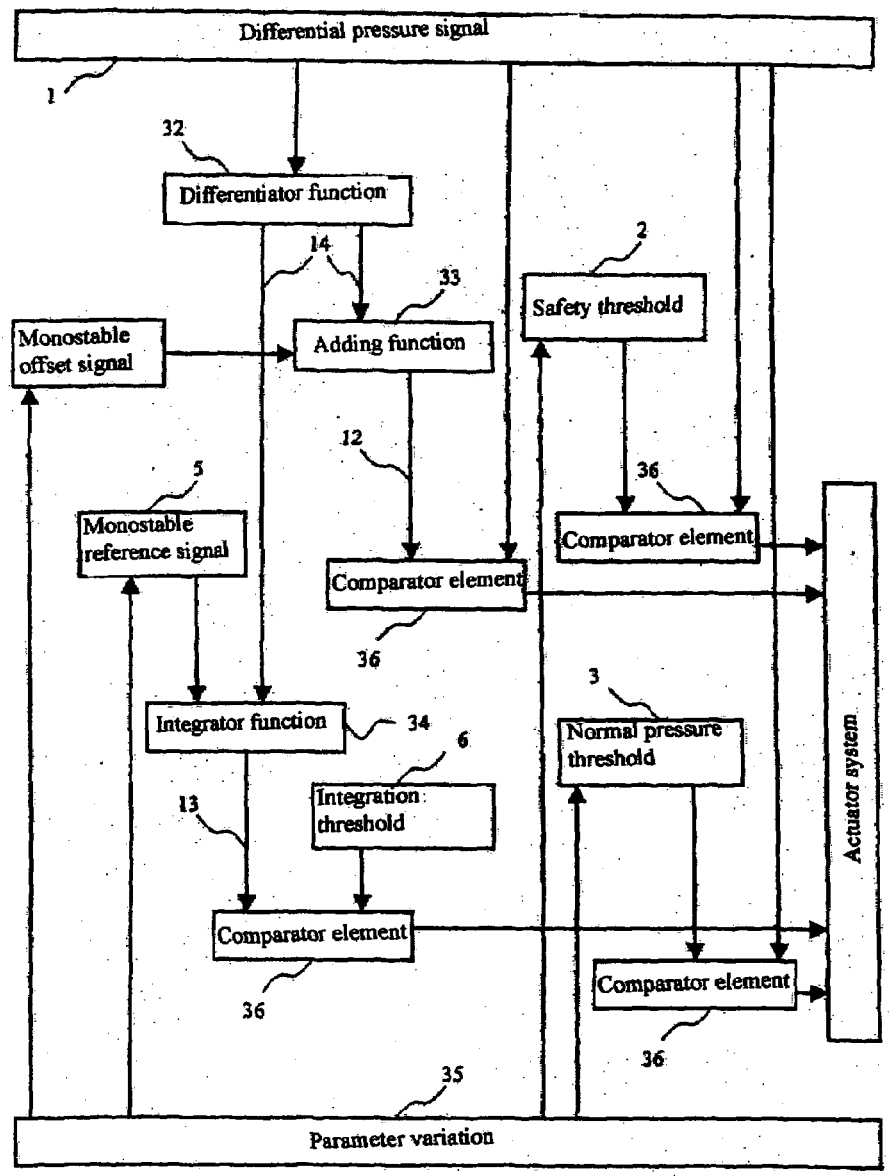
Figure 3:
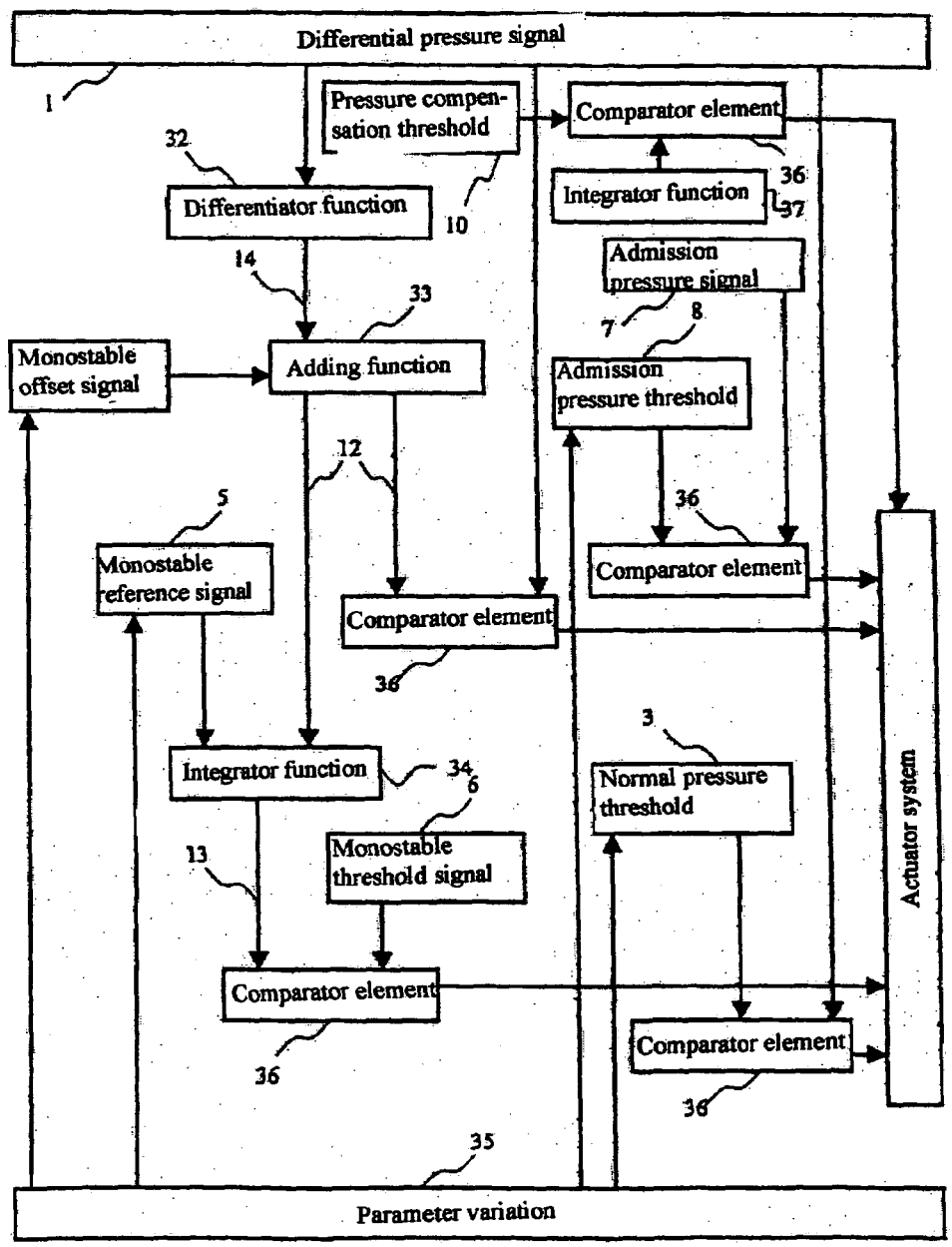
Figure 4:
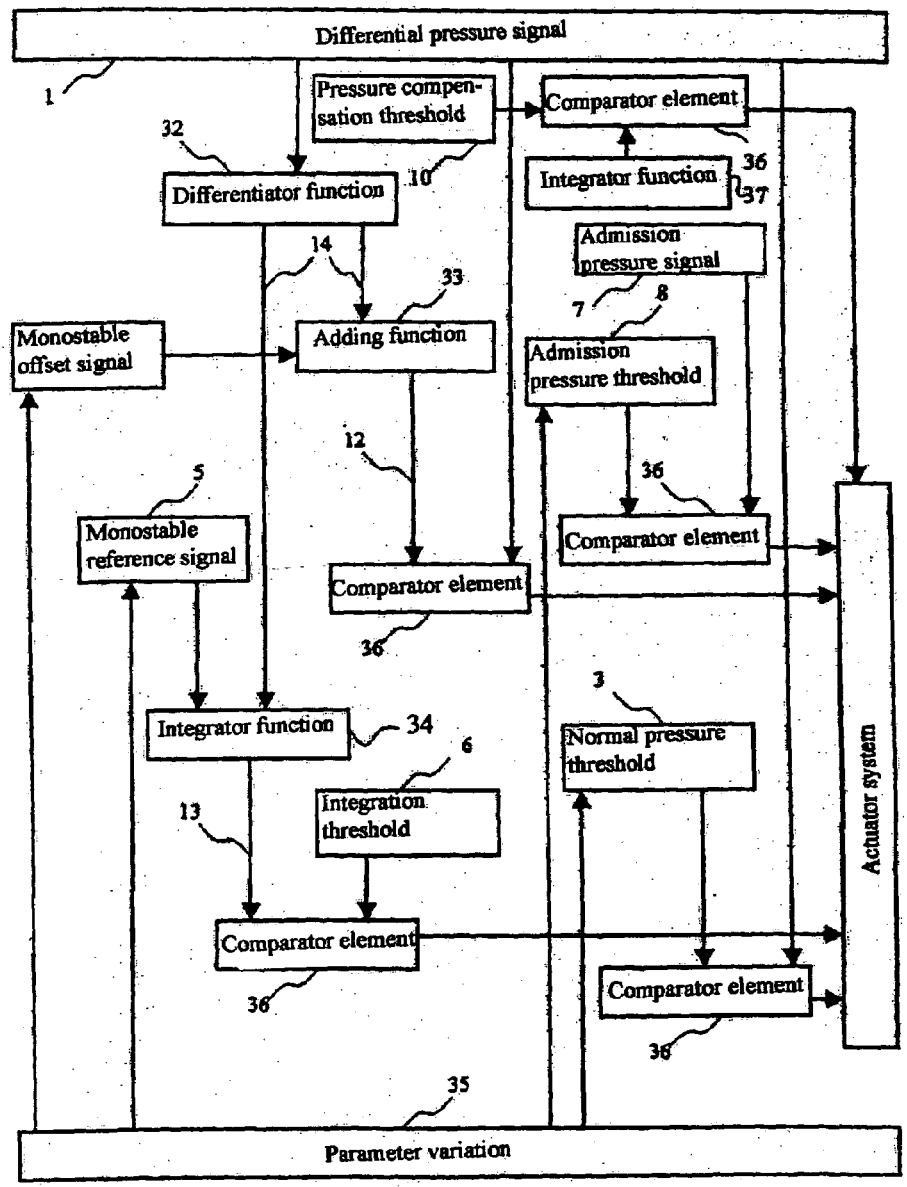
Figure 5A:
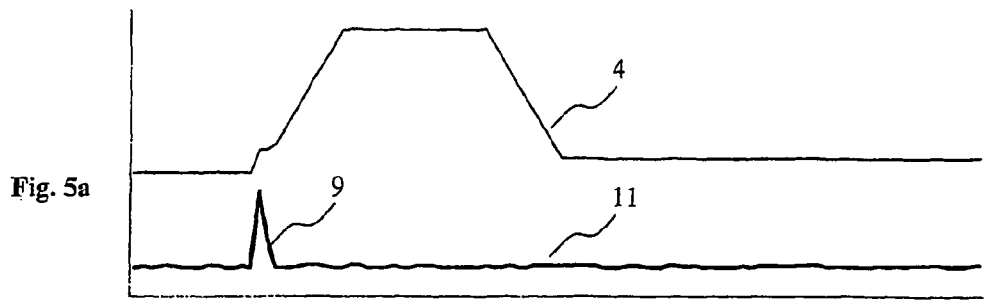
Figure 5B:
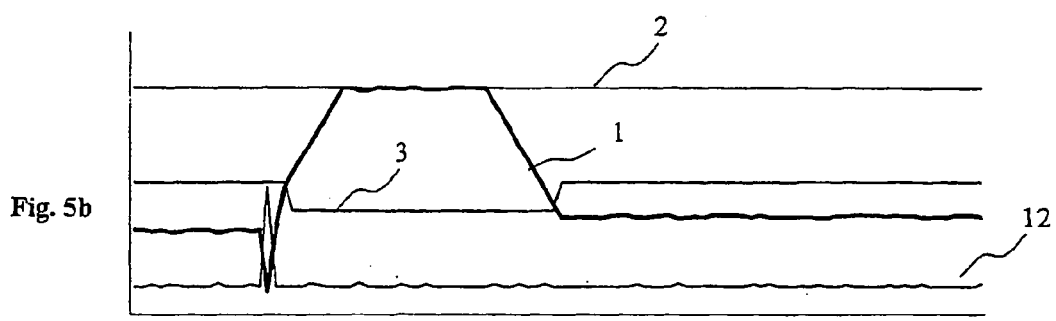
Figure 5C:
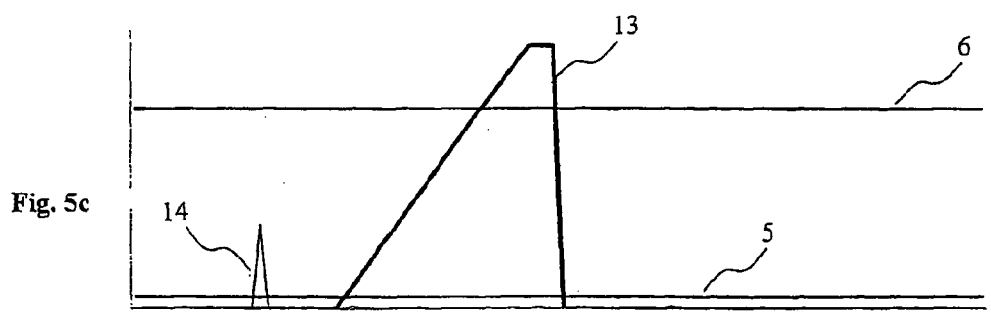
Figure 5D:
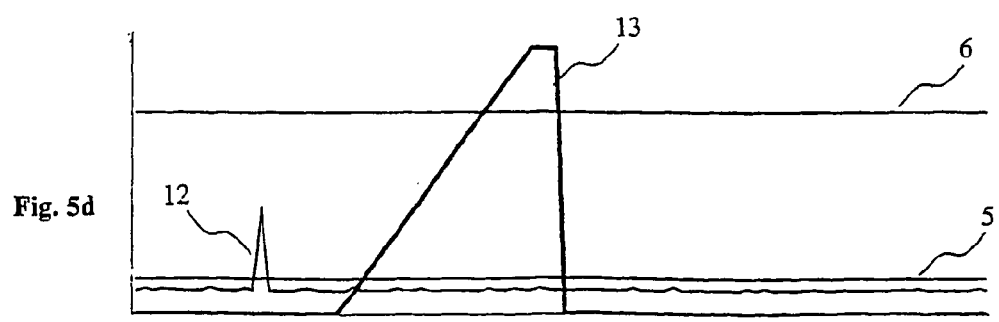
Figure 5E:
Figure 6A:
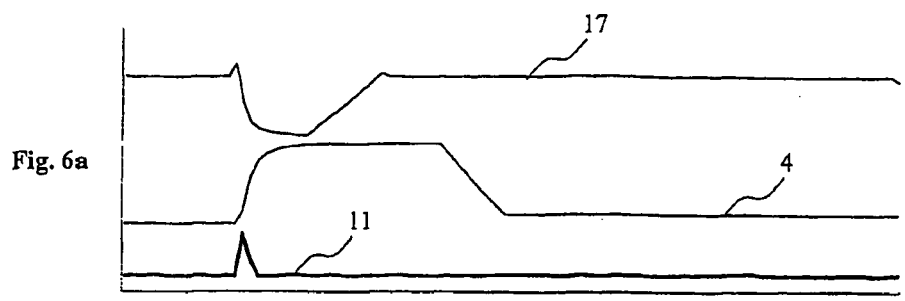
Figure 6B:
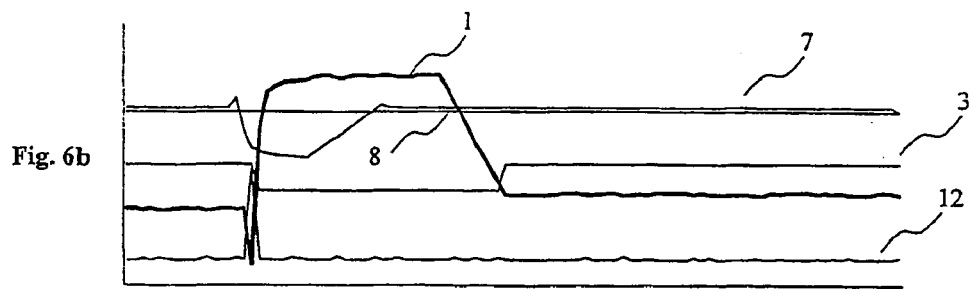
Figure 6C:
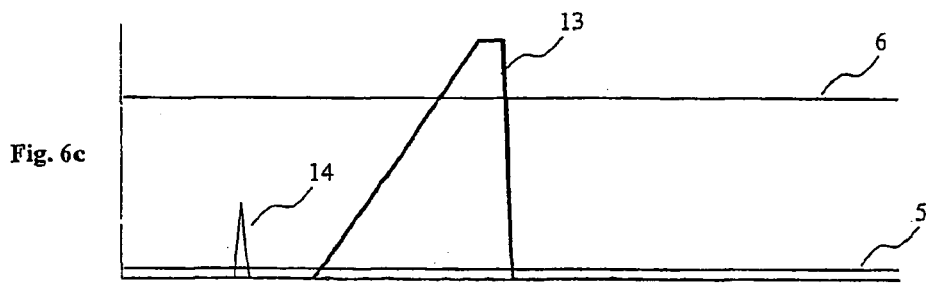
Figure 6D:
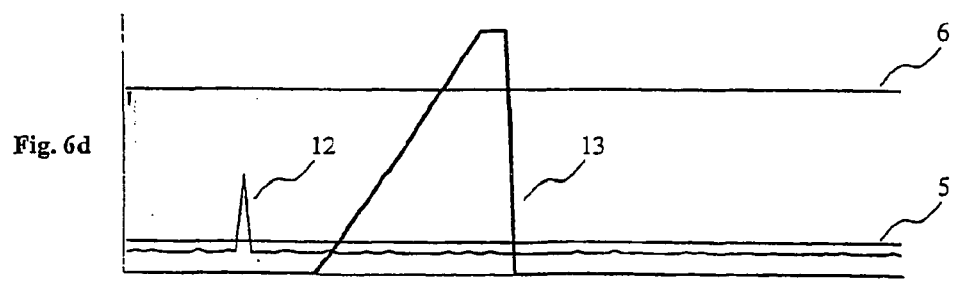
Figure 6E:
Figure 6F:
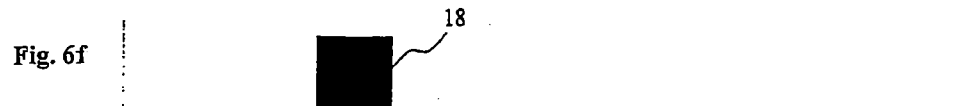
Figure 6G:
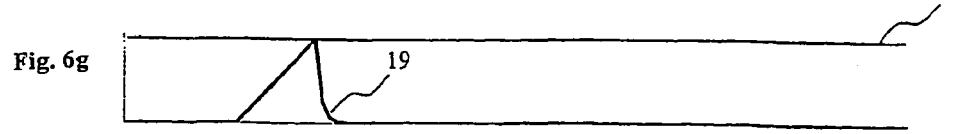
Figure 7A:
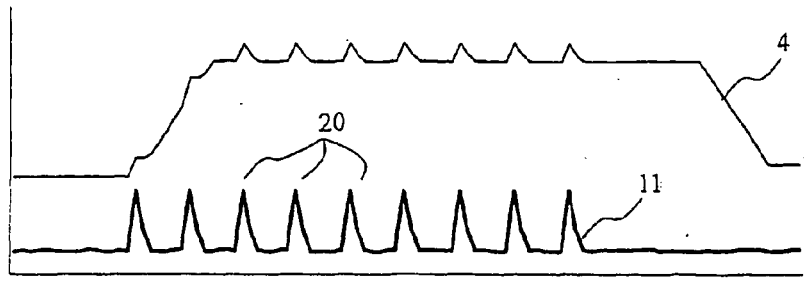
Figure 7B:
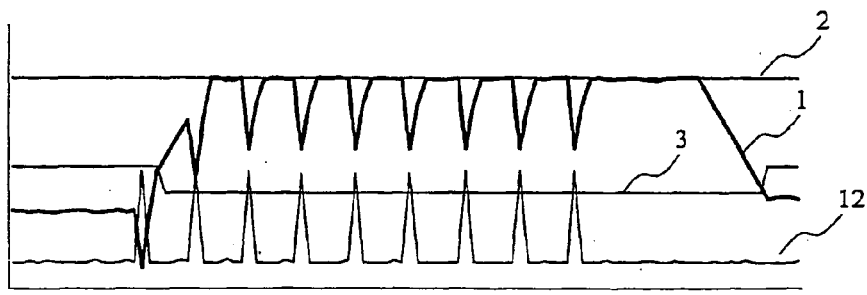
Figure 7C:
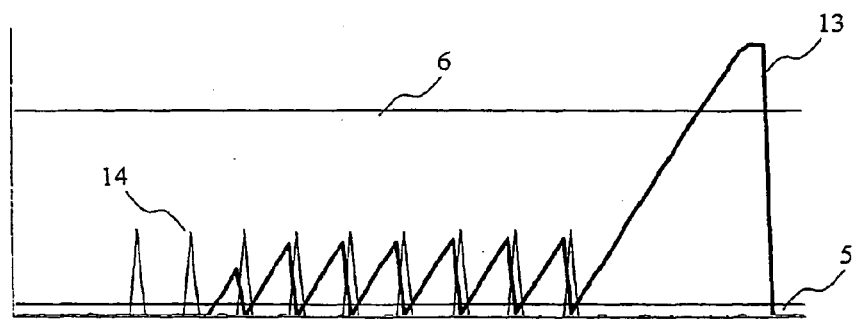
Figure 7D:
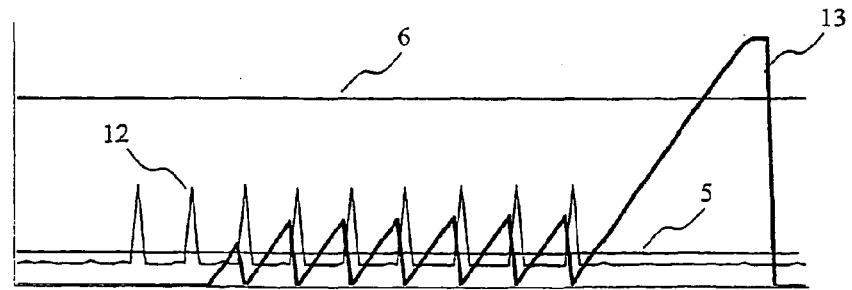
Figure 7E:
Figure 8A:
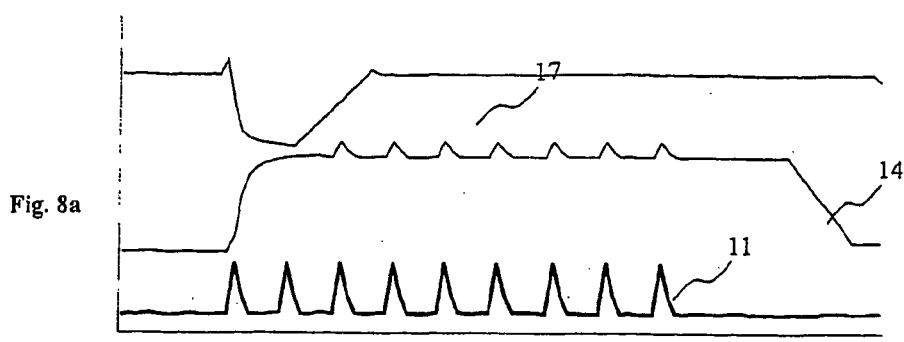
Figure 8B:
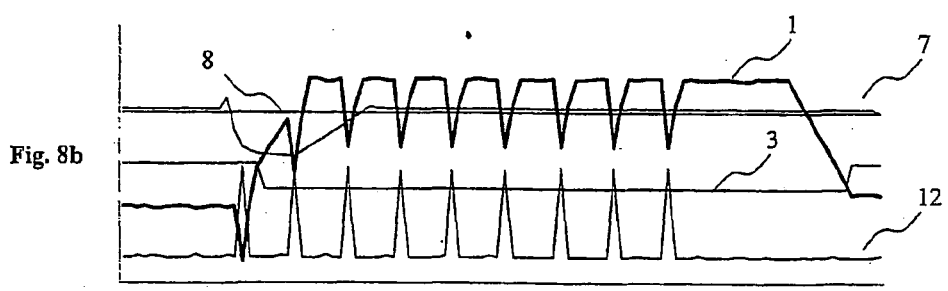
Figure 8C:
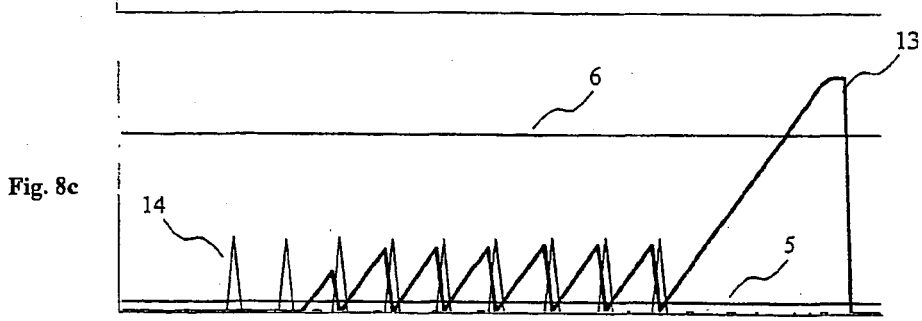
Figure 8D:
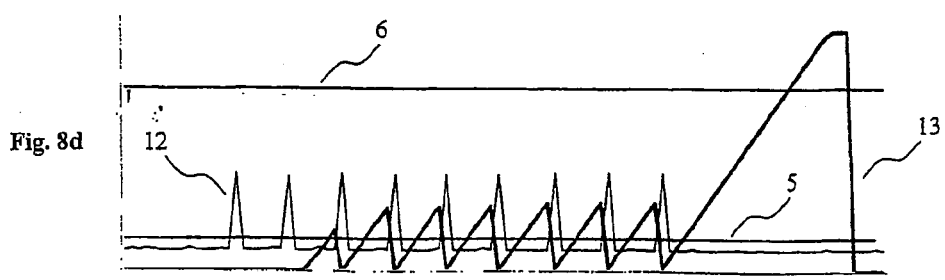
Figure 8E:
Figure 8F:
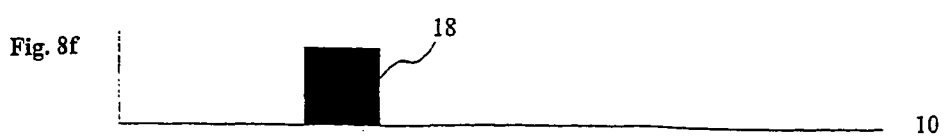
Figure 8G:
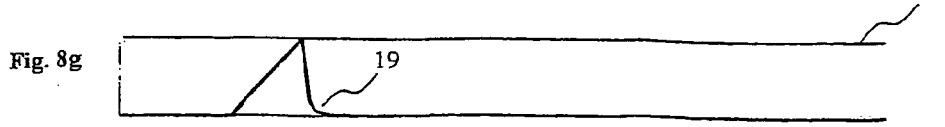
Figure 9A:
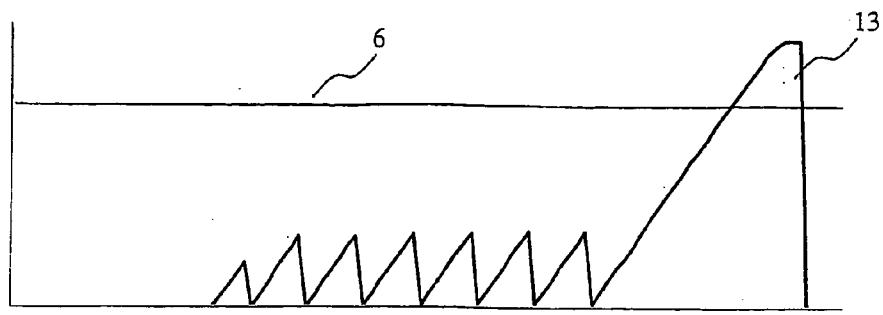
Figure 9B:
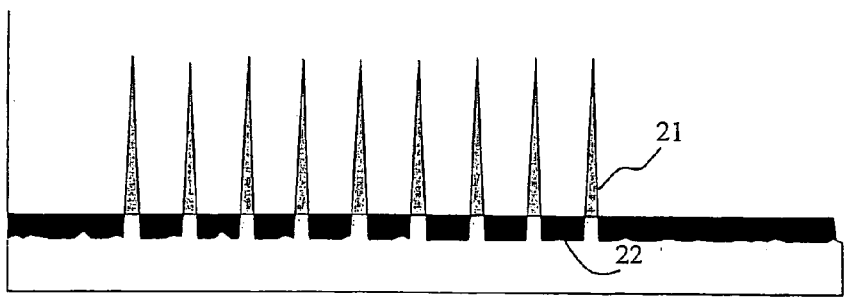
Figure 10:
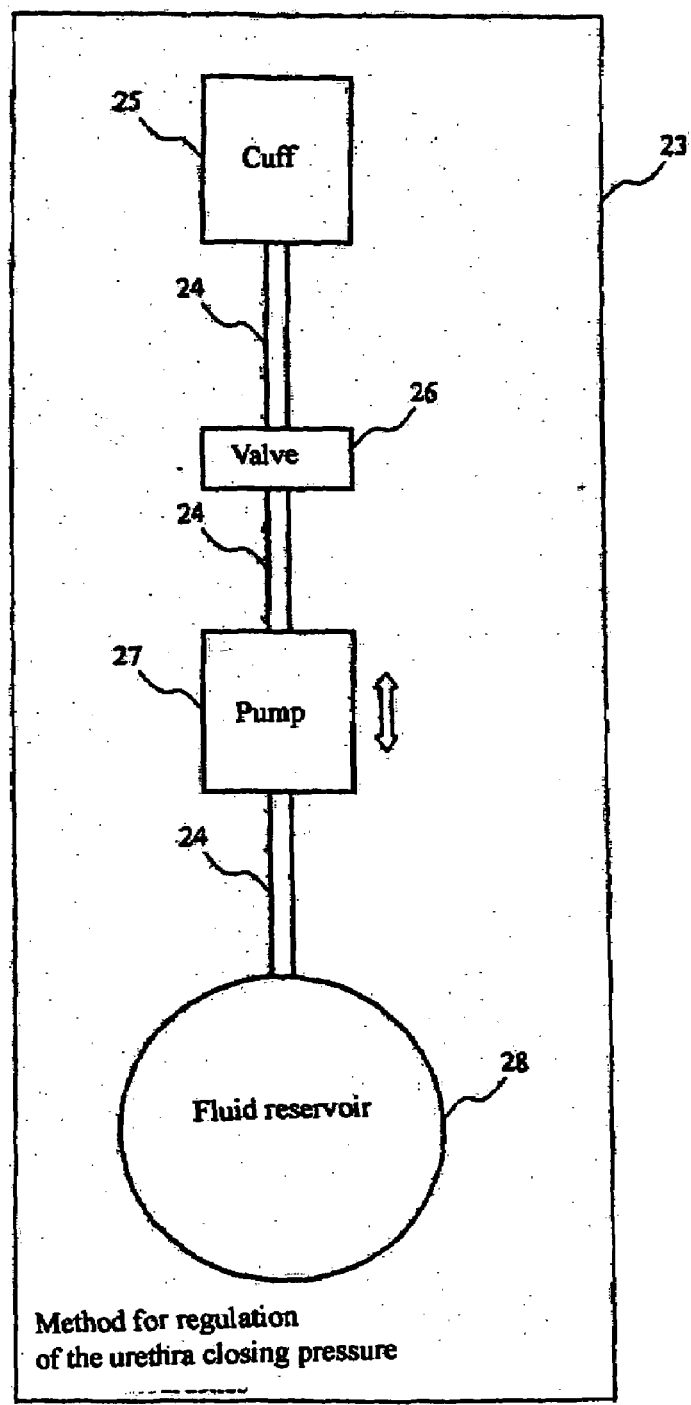
Figure 11:
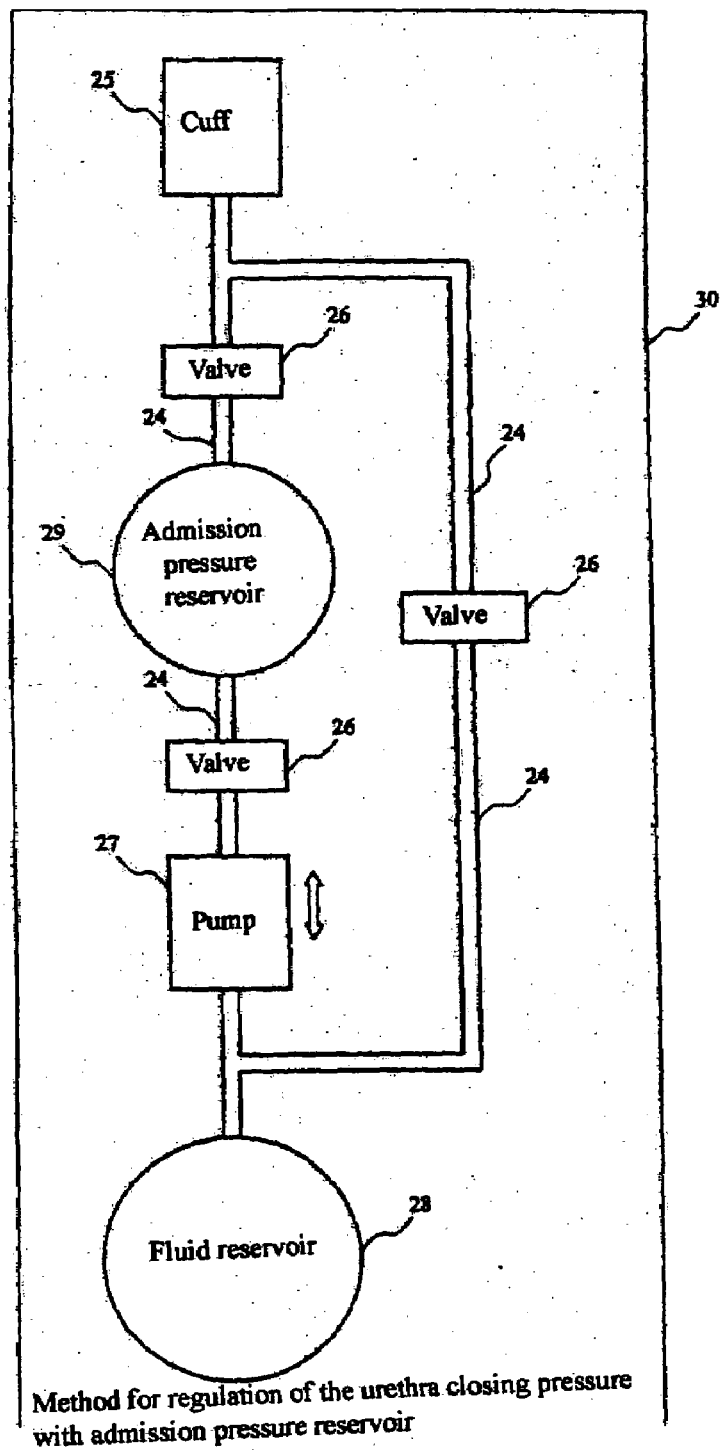
Figure 12:
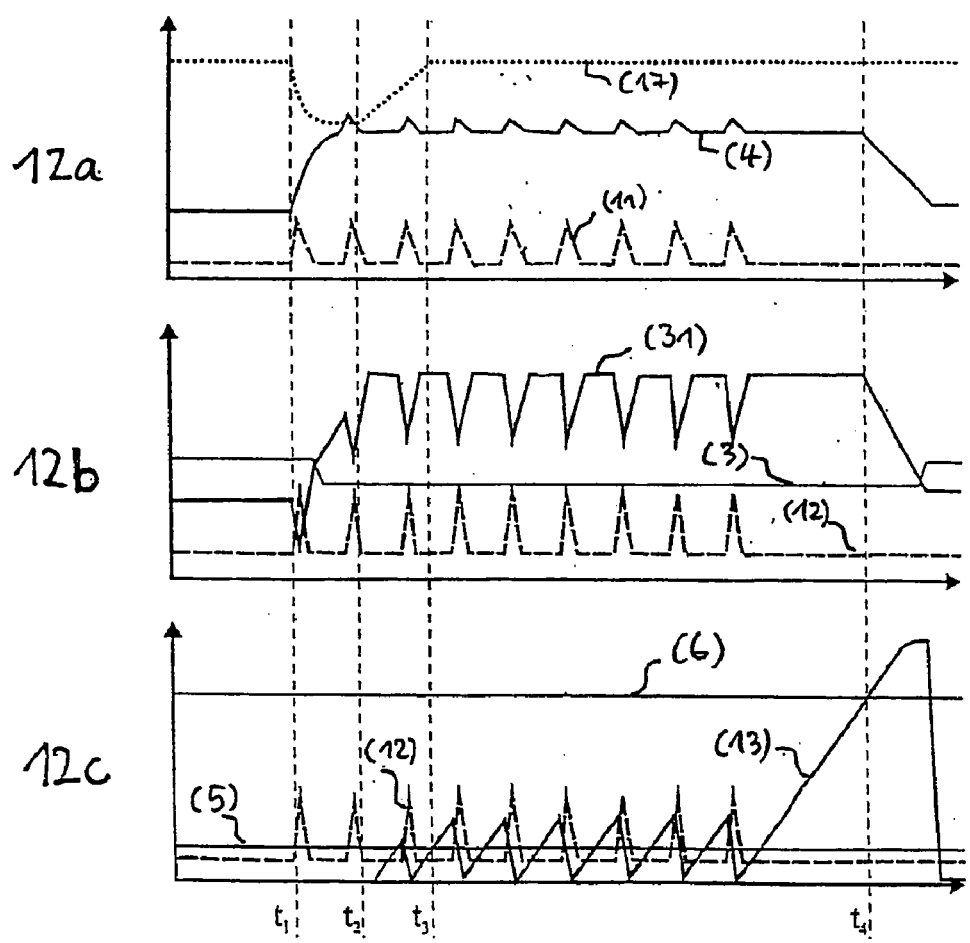
Figure 13:
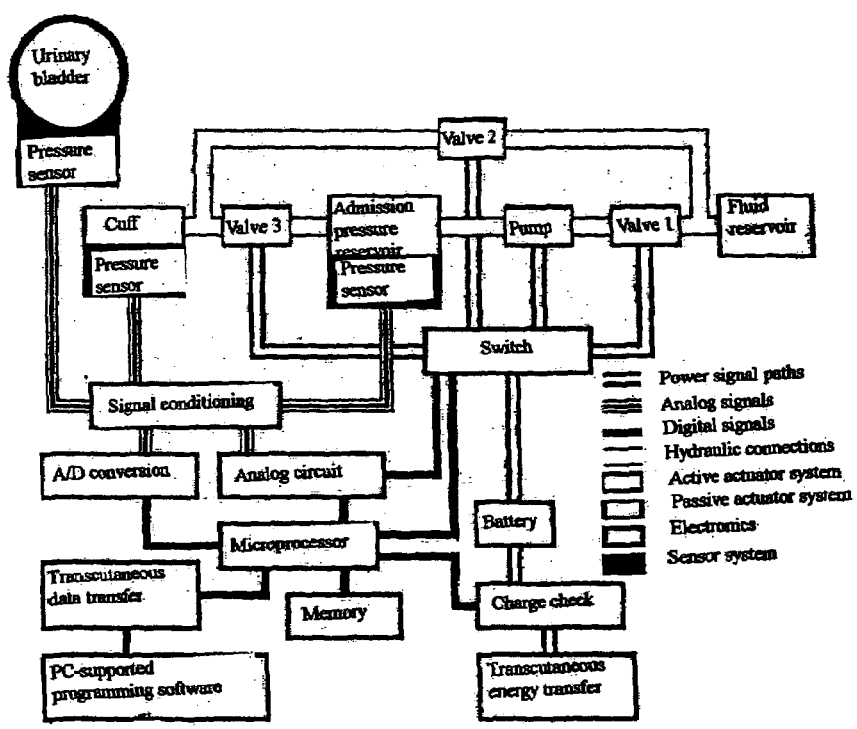

FIG. 1B: a schematic functional block diagram without admission pressure reservoir and with the output signal of the differentiator function as the input signal of the integrator function;

FIG. 2: a schematic functional block diagram without admission pressure reservoir and with the output signal of the adding function as the input signal of the integrator function;

FIG. 3: a schematic functional block diagram with an admission pressure reservoir and with the output signal of the differentiator function as the input signal of the integrator function;

FIG. 4: a schematic functional block diagram with an admission pressure reservoir and with the output signal of the adding function as the input signal of the integrator function;

FIG. 5a=FIG. 7a: with sustained dynamic strain, the pressure curve in the cuff and in the urinary bladder upon short-term dynamic strain;

FIG. 5b=FIG. 7b: with sustained dynamic strain, the signal curve of the electronic circuit upon short-term dynamic strain;

FIG. 5c=FIG. 7c: with sustained dynamic strain, the signal curve of the integrator system with the output signal of the differentiator function as the input signal of the integrator function upon short-term dynamic strain;

FIG. 5d=FIG. 7d: with sustained dynamic strain, the signal curve of the integrator system with the output signal of the adding function as the input signal of the integrator function upon short-term dynamic strain;

FIG. 5e=FIG. 7e: with sustained dynamic strain, the switching conditions for pressure increase and pressure decrease in the cuff in case of short-term dynamic strain;

FIG. 6a=FIG. 8a: with sustained dynamic strain, the pressure curve in the cuff, in the urinary bladder and the admission pressure reservoir upon short-term dynamic strain;

FIG. 6b=FIG. 8b: with sustained dynamic strain, the signal curve of the electronic circuit upon short-term dynamic strain;

FIG. 6c=8c: with sustained dynamic strain, the signal curve of the integrator system with the output signal of the differentiator function as the input signal of the integrator function upon short-term dynamic strain;

FIG. 6d=FIG. 8d: with sustained dynamic strain, the signal curve of the integrator system with the output signal of the adding function as the input signal of the integrator function upon short-term dynamic strain;

FIG. 6e=FIG. 8e: with sustained dynamic strain, the switching conditions for pressure increase and pressure decrease in the cuff upon short-term dynamic strain;

FIG. 6f=FIG. 8f: with sustained dynamic strain, the switching conditions for pressure increase in the admission pressure reservoir;

FIG. 6g=FIG. 8g: with sustained dynamic strain, the course of the integrator signal for controlling the opening of the valve between cuff and admission pressure reservoir;

FIG. 9a: the integrator signal with switching threshold upon sustained dynamic strain;

FIG. 9b: the input signals of the integrator function with areas of progressive (22) and retrogressive (21) integration upon sustained dynamic strain;

FIG. 10: the method for regulation of the urethra closing pressure without admission pressure reservoir;

FIG. 11: the method for regulation of the urethra closing pressure with admission pressure reservoir;

FIG. 12: the signal curve upon dynamic strain, namely 12a absolute pressures, 12b the urethra closing pressure signal with switching thresholds and 12c the integrator signal with switching thresholds (or, respectively, integrator system or, respectively, integrator element); and FIG. 13: a functional schematic presentation of the artificial sphincter implant.

A digital as well as analog realization of the electronic control of the sphincter implant is possible. This will not basically change the method for controlling the sphincter implant which is the subject of this invention.

By means of variable parameters, the patient is given the opportunity to individually adjust the implant behavior to personal requirements. For parameter variation with analog control, D/A converters are used whose clock signal is externally generated and can be transmitted via telemetry.

Operating Mode of the Electronic Control

The electronic control which is the subject of this invention converts fine-sensory signals, especially the differential pressure between urinary bladder and cuff or a comparable differential pressure, into control commands to the actuator system of the implant.

The sensor signals applied on the signal inputs are amplified by means of amplifier circuitry such that the signals will operate between the limit values specified by the circuitry.

During operation without dynamic strain, such as for example when calmly sitting or lying down, the cuff pressure (4) operates in a range in which the blood circulation of the urethra tissue is ensured, which could, however, easily result in incontinence upon an increase of the internal bladder pressure (11). If the differential pressure signal or, respectively, the differential pressure value (1) increases, the cuff pressure (4) will decrease (16) upon reaching a bistable threshold value (3); if the differential pressure signal or, respectively, the differential pressure value (1) drops below the lowered bistable threshold value (3), the decrease (16) of the cuff pressure (4) will be terminated. For the analog variant, this is done by means of a comparator function which is provided with a hysteresis circuit.

If dynamic strain develops, the actuator system must take over the function of a healthy sphincter, that is prevent incontinence in case of dynamic strain, through active pressure transmission, thus the involuntary contraction of the sphincter. Upon a sudden pressure increase, for example when coughing or laughing, the cuff pressure (4) must be increased within milliseconds. Since incontinence can be assumed at a differential pressure of zero, the actuator system will be caused to increase (15) the cuff pressure (4) if the differential pressure signal or, respectively, the differential pressure value (1) drops below a threshold value which is different from zero. Moreover, as a prophylactic measure against a certain inertia of the actuator system, the electronic control system is designed to provide this lower threshold value—under which the differential pressure signal or, respectively, the differential pressure value (1) may drop upon miction only—with an additive active component. To achieve this, for the analog variant of the differential pressure signal (1), it is differentiated by means of a differentiator circuit, and the output signal or, respectively, the output value (14) of the differentiator function is increased by the lower threshold value by means of an adding circuit. When using a microprocessor, the sensor signal is numerically differentiated by subtracting the current signal value from the penultimate signal value, and the result, if positive, will be added with an offset component. The result serves as the lower threshold value (12). With these measures, it will be achieved that the lower threshold value (12)—upon a sudden increase of the internal bladder pressure (11)—runs counter to the sinking differential pressure signal or, respectively, the differential pressure value (1) and thus enables early activation of the actuator system. For the analog variant, the actuator system is activated by means of a comparator which compares the differential pressure signal (1) with the lower threshold value (12).

As soon as the actuator system is activated by the differential pressure signal (1) falling below the lower threshold value (12), the comparator function is deactivated with the analog variant to avoid an excessive cuff pressure (4) in non-strained operation, and the cuff pressure (4) is increased to a value at which continence can be ensured, yet the blood circulation of the urethra tissue concerned may be impaired.

Depending on the design of the actuator system, this pressure increase may be implemented in different ways:

When using an admission pressure reservoir (29), a valve (26) is opened so that a pressure compensation can take place between the admission pressure reservoir (29) and the cuff (25). Due to the fluid flow with this pressure compensation, the admission pressure (17) set beforehand must be higher by a certain amount than the desired maximum cuff pressure, depending on the design of the cuff (25) and the admission pressure reservoir (29). The valve between the admission pressure reservoir (29) and the cuff (25) is opened time-controlled. With the analog variant, an integrator element can here be especially used which is started simultaneously with the opening of the valve and whose output signal (19) is compared by means of a comparator element with a monostable threshold value (10). When reaching parity, the valve (26) between the admission pressure reservoir (29) and the cuff (25) will be closed again and, at the same time, the increase (18) of the admission pressure (17) is started in the admission pressure reservoir (29). Activation of the integrator element which—for the analog variant—controls the decrease (16) of the cuff pressure (25), occurs either simultaneously with the opening or with the closing of the valve (26) between the admission pressure reservoir (29) and the cuff (25). The signal causing the valve (26) between the admission pressure reservoir (29) and the cuff (25) to close will trigger the increase (18) of the admission pressure (17) in the admission pressure reservoir (29). The pressure signal of the admission pressure (17) which is additionally required with the application of an admission pressure reservoir (29) will be compared—for the analog variant—with a monostable threshold value (8) by means of a comparator element and, in case of parity, a signal is triggered which causes termination of the increase (18) of the admission pressure (17). When a microprocessor is used, it will be programmed such that it will principally act like the described analog circuit.

With a differently designed actuator system without admission pressure reservoir (29), reaching this safety pressure will be registered by means of a comparator element or, respectively, a comparator function which compares the differential pressure signal or, respectively, the differential pressure value (1) with a monostable threshold value (2) and will trigger a signal when the differential pressure signal or, respectively, the differential pressure value (1) exceeds this threshold value (2) which causes the actuator system to terminate the increase (15) of the cuff pressure (4) . Moreover, this signal activates the integrator element or, respectively, the integrator function which controls the decrease (16) of the cuff pressure (4).

Activation of the integrator element which controls—for the analog variant—the decrease (16) of the cuff pressure (4) can in particular be done via the interruption of a discharge circuit of the condenser with negative feedback operational amplifier of the integrator element. Thus, integration can take place and the starting value is equivalent to the tension over the discharged condenser.

The electronic circuitry's intelligence is especially manifest in that the decrease (16) of the cuff pressure (4) will be delayed upon sustained dynamic strain. For the analog variant, an integrator element is used for this. A suitable selection of the input signals will achieve that—in case of short-term strain, for example when getting up from a sitting position—the cuff pressure (4) is relatively fast decreased again to values which correspond with a safe normal operation without the risk of necrosis. In contrast, with sustained dynamic strain—for example with physical activities—the cuff pressure (4) is kept so long at a high level until the dynamic strain abates. With the analog variant, this behavior is generated by applying two suitable signals on the inverting and non-inverting input of the operation amplifier of the integrator element. On the one hand, this is a signal which is analog to the output signal (14) of the differentiator element, especially either the output signal (14) of the differentiator element itself or the output signal (12) of the adding element. At the other input of the operation amplifier of the integrator element, there is a monostable reference signal (5). This monostable reference signal (5) is selected such that it can be crossed by the signal applied at the other input of the operation amplifier of the integrator element upon dynamic strain and thus volatile output signal (14) of the differentiator element. This circuiting of the integrator element has the consequence that the output signal (13) of the integrator element moves away from the starting point if the input signal which is analog to the output signal (14) of the differentiator element has not or rarely crossed the monostable reference signal (5), thus in case of a low dynamic of strain. In contrast, however, if the dynamic of strain is high, the input signal analog to the output signal (14) of the differentiator element frequently crosses the monostable reference signal (5). As soon as the input signal analog to the output signal (14) of the differentiator element has crossed the monostable reference signal (5), the output signal (13) of the integrator element moves toward the starting value. Thus, with a high dynamic of strain, the output signal (13) of the integrator element is driven in zigzag fashion toward the starting value. For the analog variant, a comparator element will compare the output signal (13) of the integrator element with a constant threshold value (6) which may not be in the proximity of the starting value of the output signal (13) of the integrator element. As soon as the output signal (13) of the integrator element reaches this constant threshold value (6), a decrease (16) of the cuff pressure (4) is caused. This decrease occurs due to the activation of the comparator element which causes the actuator system to decrease (16) the cuff pressure (4) until the differential pressure signal (1) falls below the lowered bistable threshold signal (3). The cuff pressure (4) is now again in a safe range where the risk of necrosis is minimal. If a microprocessor is used, it will basically perform numerically the same calculations as the analog circuit and will thus produce a comparable behavior.

Another vital characteristic of this electronic control is the presence of a plurality of possibilities to influence the system's behavior from the outside through a variation of parameters. The artificial fine-sensory sphincter implant can thereby be adjusted to the patient's individual requirements—on the one hand, setting the parameters after scarring is completed after the implantation; on the other hand, in case of changing requirements by the patient, for example with progressing age or a changed way of life.

Since, for the analog variant, the number of variable parameters must be limited as opposed to the digital variant, four parameters have been selected for the variation which can decisively influence the behavior of the implant.

The Monostable Offset Signal

The monostable offset signal is the additive component which supplements the output signal (14) of the differentiator element to the lower circuit threshold. By variation of the monostable offset signal, an excessively sluggish actuator system or a premature urine flow can be compensated.

The Bistable Threshold Signal (3)

The bistable threshold signal (3) can be varied if the cuff pressure (4) in normal operation already reaches critical values for the blood circulation of the urethra tissue, or if the bistable threshold signal (3) is adjusted so low that the decrease (16) of the cuff pressure (4) is caused unreasonably frequently.

The Monostable Reference Signal (5)

By variation of the monostable reference signal (5), the speed of integration can be adjusted.

The Monostable Threshold Signal (2)

The monostable threshold signal (2) is equivalent to the differential pressure signal or, respectively, the differential pressure value (1) at which the cuff pressure (4) has a value which ensures continence, where the blood circulation of the urethra tissue is impaired, however. If the monostable threshold signal (2) is too low, the differential pressure signal or, respectively, the differential pressure value (1) can fall below the lower circuit threshold—despite increased cuff pressure (4) in case of a high dynamic strain—and thus trigger a further pressure increase. With a monostable threshold signal (2) which is adjusted too high, the urethra tissue may be damaged due to the excessive cuff pressure (4); or The Monostable Threshold Signal (8)

By variation of the monostable threshold signal (8), the admission pressure in the admission pressure reservoir and thus the maximum cuff pressure (4) is adjusted after pressure compensation.

If a microprocessor is used, there are considerably more possibilities from the start to influence the behavior, including a completely new programming.

The Methods for Regulation of the Cuff Pressure

The actuator system controlled by the described analog circuit can avail itself of various methods and arrangements to produce the desired influence on the urethra. The different arrangements and components of the actuator system require matched control electronics. Two hydraulic methods are described hereinafter by way of example—one with and one without an admission pressure reservoir (29).

See FIG. 10, with regard to the method for a regulation of the cuff pressure (4) by means of a pump (27), a valve (26) and a fluid reservoir (28) via hydraulic connections (24).

With this method for a regulation of the cuff pressure (4), use of a pump (27) is specified which, upon standstill, puts up slight resistance to the hydraulic flow. Upon opening the valve (26) to decrease (16) the cuff pressure (4), there is a pressure compensation between the cuff (25) and the fluid reservoir (28). The valve (26) can be placed between the cuff (25) and the pump (27), as well as between the pump (27) and the fluid reservoir (28).

See FIG. 11, with regard to the method for a regulation of the cuff pressure (4) by means of a pump (27), an admission pressure reservoir (29), three valves (26) and a fluid reservoir (28) via hydraulic connections (24).

The use of an admission pressure reservoir (29) in this method enables a flash-like increase (15) of the cuff pressure (4). However, another pressure sensor will be required which controls the regulation of the admission pressure (17). After triggering the increase (15) of the cuff pressure (4), a pressure compensation will be enabled by opening the valve (26) between the admission pressure reservoir (29) and the cuff (25). Thus, the safety pressure in the cuff (25) only depends on the admission pressure (17) adjusted beforehand in the admission pressure reservoir (29). Also decisive for the pressure compensation is the design of the admission pressure reservoir (29). The smaller the dimensions, the larger the admission pressure (17) must be.

Since for the increase (18) of the admission pressure (17), the period after the increase (15) of the cuff pressure (4) is used—thus, no further increase (15) of the cuff pressure (4) can be triggered for a certain period of time—when selecting the pump (27), there need not be any high speed requirements. This will enable operation at low voltages.

Miction Control

To begin miction, a signal is generated externally. This signal causes the actuator system to decrease (16) the cuff pressure (4) and, moreover, it deactivates the analog electronic circuit except for the comparator element which limits the normal cuff pressure to the top.

After termination of miction, a second external signal is generated which again initiates the increase (15) of the cuff pressure (4). The cuff pressure (4) will be increased until the differential pressure signal or, respectively, the differential pressure value (1) reaches the bistable threshold value (3). By means of a comparator, the remaining analog electronic circuit will thus be reactivated.

In summary, this aspect of the invention thus comprises the following embodiments:

According to embodiment 1, the method for the electronic control of an artificial fine-sensory sphincter implant is characterized in that the behavior of at least one sensor signal in an analog or digital electronic circuit will be converted such by means of calculator and comparator functions and compared with reference values such that an actuator system will be controlled such that the cuff pressure or, respectively, the differential pressure between the cuff and the urinary bladder will move either in a low range, limited by two threshold values, or above a specific safety pressure.

According to embodiment 2, the sensor signal or, respectively, the sensor value (1) of the electronic circuit according to embodiment 1 is characterized in that it behaves analog the difference between the internal bladder pressure (11) and the cuff pressure (4).

According to embodiment 3, the differentiator function of the electronic circuit according to embodiment 1 is characterized in that the output signal or, respectively, the output value (14) of the differentiator function is in accordance with the differentiation of the course of the sensor signal (1) according to embodiment 2.

According to embodiment 4, the adding function with a monostable offset signal or, respectively, offset value of the electronic circuit according to embodiment 1 is characterized in that the output signal or, respectively, the output value (12) of the adding function is in accordance with the output signal or, respectively, output value (14) of the differentiator function according to embodiment 3, increased by a monostable offset signal or, respectively, a monostable offset value.

According to embodiment 5, the comparator function with a bistable threshold signal or, respectively, threshold value (3) of the electronic circuit according to embodiment 1 is characterized in that—in the event of parity or, respectively, crossing of the sensor signal or, respectively, the sensor value (1) according to embodiment 2 with the bistable threshold signal or, respectively, with the bistable threshold value (3)—this threshold signal or, respectively, this threshold value (3) will be decreased or, respectively, increased by the amount due to hysteresis and a signal will be triggered which causes the actuator system to decrease (16) the cuff pressure (4) until a signal is triggered—due to the renewed parity or, respectively, renewed crossing of the sensor signal (1) according to embodiment 2 with the bistable threshold signal or, respectively, the bistable threshold value—which causes the actuator system to terminate the decrease (16) of the cuff pressure (4) and will increase or, respectively, decrease the bistable threshold signal or, respectively, the bistable threshold value (3) by the amount due to hysteresis.

According to embodiment 6, the comparator function of the electronic circuit according to embodiment 1 is characterized in that the sensor signal or, respectively, the sensor value (1) according to embodiment 2 is compared with the output signal or, respectively, the output value (12) of the adding function according to embodiment 4 such that—in the event of parity or, respectively, crossing of the sensor signal or, respectively, the sensor value (1) according to embodiment 2 with the output signal or the output value (12) of the adding function according to embodiment 4—a signal will be triggered which causes the actuator system to increase (15) the cuff pressure (4) and deactivates the comparator function according to embodiment 5.

According to embodiment 7, the integrator function with a monostable reference signal or, respectively, a monostable reference value (5) and a constant starting value of the electronic circuit according to embodiment 1 is characterized in that optionally a) the monostable reference signal or, respectively, the monostable reference value (5) is unequal to the monostable offset signal or, respectively, the offset value according to embodiment 4 and is selected such that the output signal or, respectively, the output value (12) of the adding function according to embodiment 4 upon activity will cross the monostable reference signal or, respectively, the monostable reference value (5), and that the integrator function will continuously or numerically integrate the difference between the output signal or, respectively, the output value (12) of the adding function according to embodiment 4 and the monostable reference signal or, respectively, the monostable reference value (5) such that with a low activity of the output signal or, respectively, the output value (14) of the differentiator function according to embodiment 3, the output signal or, respectively, the output value (13) of the integrator function will move away from the starting value and upon high activity of the output signal or, respectively, the output value (14) of the differentiator function according to embodiment 3, will move toward the starting value, see FIG. 1d, FIG. 2d, FIG. 3d, FIG. 4d and FIG. 5; or b) the monostable reference signal or, respectively, the monostable reference value (5) is unequal to the output signal or, respectively, the output value (14) of the differentiator function according to embodiment 3 upon low activity and is selected such that the output signal or, respectively, the output value (14) of the differentiator function according to embodiment 3 upon activity will cross the monostable reference signal or, respectively, the monostable reference value (5), and that the integrator function will continuously or numerically integrate the difference between the output signal or, respectively, the output value (14) of the differentiator function according to embodiment 3 and the monostable reference signal or, respectively, the monostable reference value (5) such that, upon low activity of the output signal or, respectively, the output value (14) of the differentiator function according to embodiment 3, the output signal or, respectively, the output value (13) of the integrator function will continuously move away from the starting value and upon high activity of the output signal or, respectively, of the output value (14) of the differentiator function according to embodiment 3 will move towards the starting value, see FIG. 1c, FIG. 2c, FIG. 3c, FIG. 4c and FIG. 5.

According to embodiment 8, the delay function of the electronic circuit according to embodiment 1 when using a method for the regulation of the cuff pressure (4) with admission pressure reservoir (29) is characterized in that, upon triggering the pressure compensation between the admission pressure reservoir (29) and the cuff (25) by the comparator function according to embodiment 6, the delay function will be activated and upon reaching the set delay time, a signal is triggered which causes the actuator system to terminate the pressure compensation between the admission pressure reservoir (29) and the cuff (25) and activates the integrator function according to embodiment 7 such that, upon activation, the output signal or, respectively, the output value (13) of the integrator function according to embodiment 7 is in accordance with the constant starting value according to embodiment 7.

According to embodiment 9, the comparator function with a monostable threshold signal or, respectively, threshold value (2) of the electronic circuit according to embodiment 1 is characterized in that—in the event of parity or, respectively, crossing of the sensor signal or, respectively, sensor value (1) according to embodiment 2 with the monostable threshold signal or, respectively, the monostable threshold value (2)—a signal is triggered which causes the actuator system to terminate the increase (15) of the cuff pressure (4) and activates the integrator function according to embodiment 7 such that, upon activation, the output signal or, respectively, the output value (13) of the integrator function according to embodiment 7 will be in accordance with the constant starting value according to embodiment 7.

According to embodiment 10, the comparator function with a monostable threshold signal or, respectively, a monostable threshold value (6) of the electronic circuit according to embodiment 1 is characterized in that—in the event of parity or, respectively, crossing of the output signal or, respectively, the output value (13) of the integrator function according to embodiment 7 with the monostable threshold signal or, respectively, threshold value (6)—a signal is triggered which causes the actuator system to decrease (16) the cuff pressure (4) and/or activates the comparator function according to embodiment 5.

According to embodiment 11, the monostable offset signal or, respectively, the monostable offset value according to embodiment 4 is characterized in that it can be varied by parameter variation from the outside.

According to embodiment 12, the bistable threshold signal or, respectively, the bistable threshold value (3) according to embodiment 5 is characterized in that it can be varied by parameter variation from the outside.

According to embodiment 13, the monostable reference signal or, respectively, the monostable reference value (5) according to embodiment 7 is characterized in that it can be varied by parameter variation from the outside.

According to embodiment 14, the monostable threshold signal or, respectively, the monostable threshold value (2) according to embodiment 9 is characterized in that it can be varied by parameter variation from the outside.

According to embodiment 15, the method of the electronic circuit for the control of miction according to embodiment 1 is characterized in that, for activation of miction, an external signal causes the actuator system to decrease the urethra closing pressure and deactivates the electronic circuit according to embodiment 1 expect for the comparator function according to embodiment 5, and for deactivation of miction, an external signal causes the actuator system to increase (15) the cuff pressure (4) until a signal is triggered—in the event of parity or, respectively, crossing of the sensor signal (1) according to embodiment 2 with the bistable threshold signal or, respectively, threshold value (3) according to embodiment 5—which activates the electronic circuit according to embodiment 1.

This invention presents a novel fine-sensory implant which combines the most important aspects of technological issues of in vivo medical technology: a reliable fine sensory system; intelligent, flexible control electronics with low power consumption; a miniaturized and powerful actuator system, as well as sophisticated energy and data transmission. Using this implant as an example—an artificial, adaptive, fine-sensory sphincter—the current state of the art of implantation technology will be discussed before the background of its development history and the methodical development of criteria for selection control and alternative design, including intensive tests for the determination of individual components, simultaneously taking comparable implants into account.

Numbers in brackets refer to the places found in the bibliography at the end of this description. The references refer to FIGS. 12a to 12c.

A current system of an artificial bladder neck sphincter, for example the AMS 800, uses a hand pump in the scrotum or, respectively, the labia majora, which is used to pump up the collar which blocks the flow of urine and is placed around the urethra [6]. The setting of the urethra closing pressure is problematical with this system. Insufficient pressure results in involuntary discharge of urine upon dynamic strain which can be caused by laughing, coughing, sneezing or heavy lifting. Excessive pressure on the urethra over a long period of time can readily result in black tissue, i.e. necrosis. To avoid this risk, the practice has so far been to rather accept a slight strain incontinence with all its negative social consequences.

The artificial fine-sensory sphincter implant which has been developed in accordance with the invention replaces the hand pump by active hydraulics, equipped with a fine sensory system and intelligent controls. This system can support or replace active pressure transmission. The sensory system primarily monitors the difference between internal bladder pressure and cuff pressure. In case of dynamic strain, the actuator system is used to increase the cuff pressure so that continence will be ensured even at these increased pressure conditions. Normal blood circulation of the urethra tissue can thereby be impaired for a short term. The implant is able to distinguish between single-action strain and sustained dynamic strain.

Control

The decisive factor for the function of the artificial fine-sensory sphincter implant is the urethra closing pressure (31). If the urethra closing pressure (31) is negative, urine discharge will occur.

The signal which is equivalent to the urethra closing pressure (31) is ascertained from the two absolute pressure signals of the cuff (25) and the urinary bladder (FIG. 12a). In case of suddenly arising dynamic strain in the peritoneal cavity, this signal goes fast toward zero. To ensure a fast reaction of the implant in this situation, the following measures are taken:

Lowering of the urethra closing pressure (31) is limited toward the bottom by a switching threshold which is above the incontinence range and can be varied in programming.

The response of the urethra closing pressure (31) will be differentiated and the positive portion added to the lower switching threshold (12). The faster the urethra closing pressure (31) decreases, the sooner the implant's actuator system will be activated on the basis of this measure ($t_1$) (FIG. 12b).

This time-critical area is realized by means of analog electronic components to enable maximum reaction speed. The actuator system is activated by means of a comparator which compares the signal of the urethra closing pressure (31) with the lower switching threshold (12).

The use of an admission pressure reservoir enables a flash-like reaction of the actuator system with little supply voltage. After termination of the pressure compensation ($t_2$), the admission pressure (17) is increased to a variable maximum value $p_{max}$ (within $t_2$ to $t_3$).

After termination of the dynamic strain, the increased cuff pressure is decreased, microprocessor-controlled, under the normal pressure threshold (3) provided with a hysteresis. To obtain a measure for the dynamic strain, the difference of an offset value (5) which can also be varied in programming, and the lower switching threshold (12) will be integrated. Thus, with a sustained dynamic strain, the integration result (13) is pressed downwardly in zigzag shape. Without dynamic strain, the integration result (13) increases up to a threshold value (6), and when this is reached, the reduction of the cuff pressure will be triggered ($t_4$) (FIG. 12c).

The normal pressure threshold prevents an excessive cuff pressure in normal operation. Like the activation of the actuator system, this function will also be realized with analog electronic components.

The analog circuit comprises 4 variable parameters which are influenced by means of D/A converters, namely: the speed of differentiation of the urethra closing pressure signal, the additive offset component of the lower threshold value, as well as the mean value and the hysteresis of the normal pressure threshold. Thus, the permanently activated electronics will be limited to a minimum of 6 operation amplifiers and a quad-digital potentiometer of the analog circuit, as well as to the signal conditioning and the RF receiver module. The electronics complete power consumption is under 0.1 mW, with the microprocessor in power-down mode.

Programming Software

The artificial fine-sensory sphincter implant according to the invention is programmed by means of an external programming station. Via a bi-directional transcutaneous data transfer, the urethra closing pressure as well as the absolute pressure in the admission pressure reservoir are transmitted into the programming station. The in vivo pressure measurement, in combination with a simultaneous external urodynamic examination enables largely automated implant programming. The patient performs defined physical actions; for example, getting up from a sitting position or coughing. From the collected measuring data together with empirical values from clinical tests, the software can evaluate an optimal setting of the implant. Subsequently required adjustments of the programming are also manually possible, for example with regard to the patient's changed living conditions or a changed behavior of the implanted electronics.

Sensory System

Proper functioning of the artificial sphincter implant requires the use of three pressure sensors which must measure the pressure at different places and with different prerequisites:

In the admission pressure reservoir, use of a surface sensor suggests itself which can be integrated into the rigid base plate of the admission pressure reservoir. This capacitive pressure sensor consists of a polysilicon membrane and a silicon substrate [1]. During manufacture, a vacuum is produced between the polysilicon membrane and the silicon substrate so that an absolute pressure sensor is developed. With the minor diameter of 100–120 μm of a sensor element, a sensor array connected in parallel can be set up for signal amplification [2].

When using an absolute pressure sensor in the admission pressure reservoir, the absolute pressure in the cuff can also be measured by means of a differential pressure sensor which measures the difference between cuff and admission pressure. By means of a suitable electronic circuit, the absolute pressure signal of the cuff pressure can be filtered from the absolute pressure signal of the admission pressure reservoir and the differential pressure signal between cuff and admission pressure reservoir. This enables the use of an inexpensive and reliable piezo-resistive differential pressure sensor which is connected via hydraulic connections with the admission pressure reservoir as well as with the cuff.

To measure the internal bladder pressure, an absolute pressure sensor—similar to a brain pressure probe—is embedded in the tissue in the vicinity of the bladder so that the urinary bladder need not be punctured or opened [5]. The measured pressure will possibly not be exactly the same as the internal bladder pressure but it will be equivalent.

Electronics

In the artificial sphincter implant, the physical dimensions as well as the power consumption of the electronic components are not the critical parameters since both are negligible in comparison with the properties of the actuator system. Nonetheless, minimization is aimed at although more importance may be attached to reliability and redundant systems.

With regard to the requirements, the control electronics specified for the artificial fine-sensory sphincter implant are similar to those of a modern pacemaker. As in a pacemaker, sensor signals from a microprocessor are analyzed and converted into implant actions. To minimize the electronics power consumption, the microprocessor is normally operated in power-down mode. The comparator which activates the actuator system upon dynamic strain simultaneously activates the microprocessor.

The use of a microprocessor programmable via transcutaneous data transmission has the fundamental advantage that it can flexibly react to any changes, for example in the patient's habits or in the behavior of electronic components. The use of analog semiconductor components, for example as a calculator circuit to determine the absolute cuff pressure, will thus be less critical.

With a power consumption of under 1 μA per operation amplifier, the analog components can be permanently activated without any problem. The only intermittently active microprocessor can be operated with relatively high clock frequencies since the connected relatively high power consumption can be easily compensated by a considerably improved performance of the implant.

While a condenser charged with up to 1 kV must be operated with a pacemaker (usually by means of IGBTs) which discharges via the human tissue between the electrodes with several ten amperes within several milliseconds, for the artificial fine-sensory sphincter implant, maximum permanent currents of approx 100 mA per switch must be operated at a supply voltage of 4.2 V. MOSFETs suggest themselves for this purpose which can be directly operated from the microprocessor. To ensure reliability, several MOSFETs are switched in parallel per switch unit so that the switching duty can still be handled without problems if individual components fail. They can be integrated in a multi-chip module (MCM).

The signal conditioning, the analog circuit, the A/D converter, the internal memory and the microprocessor with a multi-I/O module can be combined in a mixed signal ASIC, an application-specific integrated circuit [4]. This offers extremely low power consumption since—in contrast to the use of a commercial microprocessor—no unused features lie fallow yet still use power. This advantage is confronted with high development expenditures which lead to the desired result via design, simulation and manufacturing. For this reason, the implant prototype is realized with a commercial microcontroller. The development of an ASCI for a prototype would be a disproportionately high expenditure of time and finances.

As a rule, the source of energy is a lithium-ion accumulator which is charged via a subcutaneously implanted induction coil. The charge controller of the lithium-ion battery pack is a commercial IC as it is used for example in mobile phones. It monitors the current flow between the energy transfer module and the battery which it can influence with a MOSFET. Termination, abort and fault will be reported to the microprocessor.

ACTUATOR SYSTEM

The miniaturization of implantable actuator systems requires components complying with the high requirements of modern medical technology, such as bio-compatibility, long life and reliability. In implantation medicine, silicones and polyurethanes are among the most frequently used materials which are distinguished for their compatibility with the human body. Mechanical as well as thermal endurance tests demonstrated that silicones and polyurethanes have absolutely equivalent properties. With more than 5 million load cycles, their durability for use in humans was simulated and confirmed.

The actuator system of the artificial fine-sensory sphincter implant consists of electrically active components, the valves and the pump, and of passive components, an admission pressure chamber, an inflatable cuff and the hydraulic connections (FIG. 13). These components must be specially adapted for use in the artificial fine-sensory sphincter implant. Industrial pumps and valves are mostly designed for pressures of 10 bar and more. Since maximum pressures of under 500 mbar occur in the implant, adjusted dimensioning of these components makes good sense.

The admission pressure reservoir consists of a rigid base plate over which an elastic membrane is stretched. Due to the flat structure, the admission pressure reservoir can be integrated into the outer shell of the implant such that the elastic membrane can bulge outwardly in case of a pressure increase.

The decisive function of the artificial fine-sensory sphincter implant is the flash-like increase of the cuff pressure in case of a sudden drop in the urethra closing pressure. To keep the time between activation of the actuator system and reaching a safe cuff pressure as short as possible, an increased admission pressure will be provided which can be transmitted to the cuff via valve 3. Since the electronic system reaches reaction times within the microsecond to nanosecond range, the decisive gain in reaction time is to be expected with an optimization of the system of admission pressure reservoir, valve 3 and the hydraulic connection. If, for example, a flow of 0.2 ml will be required to increase the cuff pressure from 70 mbar to 100 mbar, and the pressure difference between cuff and admission pressure reservoir is $\Delta p$ before the pressure compensation, the following proportionality will result with an opening radius of the hose r (equation 1):

$$t \sim \frac{1}{r^2 \cdot \Delta pf}$$

Reaction times of under 10 ms are realizable from activating the actuator system until termination of the pressure compensation. Required will be a pressure difference of $\Delta p=400$ mbar and an inside radius of the hydraulic connections of approx. $r=1.0$ mm. Still shorter reaction times can be realized with a further enlargement of the inside radius r.

Moreover, the mass inertia of the valve 3 will cause a further delay which increases with an increasing opening radius r.

The cuff pressure is reduced via valve 2 in the reservoir. When dimensioning the valve 2 and the hydraulic connections between cuff and reservoir, care must be taken that the cuff pressure is not reduced too fast. If this is the case, increase of the cuff pressure can be immediately triggered again due to the valve inertia and the oncoming lower switching threshold. However, this risk can be avoided with an appropriate selection of the cross-section opening of the hydraulic connections.

Energy and Data Transmission

With regard to the energy and data transmission, it has the most things in common with the artificial urinary bladder [6] [7] [8]. Other than for example with the artificial heart, the energy transmission for the artificial fine-sensory sphincter implant only serves to load the implanted battery and data transmission is mainly used for programming the microprocessor. Moreover, for miction control, another signal path is used which is uncomplicated to operate for the patient. From these framework conditions, the following configuration of energy and data transmission was designed for use in the artificial fine-sensory sphincter implant:

The implanted battery is charged inductively by placing a charger onto a subcutaneously implanted induction coil [3]. To enable fast bi-directional data transmission, an IR sending/receiving module was placed in the middle of the induction coil. This optical data transmission requires—like inductive energy transmission—that the external counterpart is placed directly on the skin.

Thus, this function can be integrated into the external charger.

The miction is controlled via unidirectional RF data transmission. This enables the patient a comfortable and uncomplicated operation of the implant. Transmitted will be the miction desire as well as a signal for terminating miction.

Results

By means of a suitable design of the actuator system, as well as an appropriate design of the electronics, a flash-like reaction of the hydraulic system was achieved with the low supply voltage of 4.2 V and the complex behavior of the electronics with the low power consumption of under 0.1 mW in the power-down mode of the microprocessor. The behavior of the implant is designed so variably that it will be able to meet a tremendously broad range of requirements.

Bibliography

[1] M. Kandler, J. Eichholz, Y. Manoli, W. Mokwa, "CMOS compatible capacitive pressure sensor with readout electronics", International Conference on Micro Electro, Opto, Mechanic Systems and Components, Micro System Technologies, pp. 574–580, 1990
[2] H. Dudaicevs, Y. Manoli, W. Mokwa, M. Schmidt, E. Spiegel, "A fully integrated surface micromachined pressure sensor with low temperature dependence", Transducers, Digest of technical papers, pp. 616–619, 1995
[3] H. Wassermann, "Drahtlose Energie- und Signalübertragung mit gleichzeitiger Disloziervorkehrung und -vorrichtung bei Unzugänglichkeit einer Seite und bei undurchsichtigem Dielektrikum", Technisches FB-Kompendium, 1992
[4] R. Lerch, E. Spiegel, R. Kakerow, R. Hakenes, H. Kappert, H. Kohlhaas, N. Kordas, M. Buchmann, T. Franke, Y. Manoli, J. Müller, "A programmable mixed-signal ASIC for data-acquisition systems in medical implants", International Solid-State Circuits Conference, Digest of technical papers, pp. 160–161, 1995
[5] A. Atala, M. R. Freeman, J. P. Vacanti, J. Shepard, A. B. Retik, "Implantation in vivo and retrieval of artificial structures consisting of rabbit and human urothelium and human bladder muscle", J. Urol. 150, pp. 608–612, 1993
[6] D. Jocham and K. Miller "Praxis der Urologie II", Stuttgart: Georg Thieme, 1994/2002
[7] H. Wassermann, "Künstliches harnableitendes System", Medizintechnik in Bayern, vol. 2, pp. 57–61, 2002
[8] R. Stölting, "Künstliche Harnblase—Klinische Tests stehen noch aus", medizin report, vol 2, pp. 22–23
[9] H. Wassermann, "Artificial Urinary Diversion System", Bavarian Medical Technologies, vol. 2, pp. 53–57, 2002

The invention claimed is:

1. A method for the electronic control of an artificial fine-sensory sphincter implant comprising:
   closing the sphincter of a bladder using a cuff having a cuff pressure;
   creating a sensor signal according to the differential between the internal bladder pressure and the cuff pressure;
   electronically comparing the differential pressure with a threshold value;
   controlling the cuff pressure so as to maintain the differential pressure between the cuff pressure and the internal bladder pressure within an upper threshold value and a lower threshold value; and
   selectively and temporarily increasing the cuff pressure above the upper threshold value in response to increases in the internal bladder pressure.

2. A method according to claim 1, wherein the steps of electronically comparing the differential pressure and controlling the cuff pressure are performed, at least in part, by an electronic circuit comprising:
   (a) a differentiator function whose output signal is equivalent to the differentiation of the curve of the sensor signal;
   (b) an adding function with a monostable offset signal whose output signal is equivalent to the output signal of the differentiator function, increased by the monostable offset signal;
   (c) an integrator function with a monostable reference signal and a constant starting value where selectively
      (i) the monostable reference signal is not equal to the monostable offset signal of the adding function and will be selected such that the output signal of the adding function upon activation crosses the monostable reference signal, with the integrator function continuously integrating the difference between the output signal of the adding function and the monostable reference signal such that, upon low activity of the output signal of the differentiator function, the output signal of the integrator function moves away from the starting value of the integrator function, and in case of high activity of the output signal of the differentiator signal will move toward the starting value, or
      (ii) the monostable reference signal is unequal to the output signal of the differentiator function upon low activity and is selected such that the output signal of the differentiator function upon activity will cross the monostable reference signal, with the integrator function numerically integrating the difference between the output signal of the differentiator function and the monostable reference such that, upon low activity of the output signal of the differentiator function, the output signal of the integrator function will continuously move away from the starting value and, upon high activity of the output signal of the differentiator function will move towards the starting value;
   (d) a comparator function with a bistable threshold signal, whereby in the event the sensor signal crosses the bistable threshold signal, the threshold signal will be changed by the amount due to hysteresis and a signal is thus triggered which causes the actuator system to decrease the cuff pressure until, the sensor signal again crosses the bistable threshold signal, a signal will be triggered which causes the actuator system to terminate the decrease of the cuff pressure and change the bistable threshold signal by the amount due to hysteresis; and
   (e) a comparator function with a monostable threshold signal, whereby, in the event the sensor signal crosses the monostable threshold signal, the increase of the cuff pressure is terminated and the integrator function activates such that, the output signal of the integrator function is in accordance with the constant starting value.

3. A method according to claim 2, wherein the sensor signal is compared with the output signal of the adding function such that, in the event the sensor signal crosses the output signal of the adding function, the cuff pressure is increased and the comparator function having the bistable threshold function is suspended.

4. A method according to claim 2, wherein, in the event the output signal of the integrator function crosses the monostable threshold signal, the cuff pressure decreases and the comparator function having a bistable threshold is activated.

5. A method according to claim 2, further comprising:
   initiating a pressure compensation between a pressure reservoir and the cuff;
   delaying termination of the pressure compensation by a set delay time; and
   upon reaching the set delay time, terminating the pressure compensation between the pressure reservoir and the cuff and activating the integrator function such that, upon activation the output signal of the integrator function is equivalent to the constant starting value.

6. A method according to claim 2, wherein the monostable offset signal may be varied by a parameter variation initiated externally.

7. A method according to claim 2, wherein the bistable threshold signal may be varied by a parameter variation initiated externally.

8. A method according to claim 2, wherein the monostable reference signal may be varied by a parameter variation initiated externally.

9. A method according to claim 2, wherein the monostable threshold signal may be varied by a parameter variation initiated externally.

10. A method according to claim 6, wherein the parameter variation is achieved via infrared transmission.

11. A method for the control of miction of the electronic circuit according to claim 1, further comprising:
   receiving a first external signal;
   activating the actuator system to decrease the cuff pressure;
   deactivating the electronic circuit, except for the comparator function having a bistable threshold;
   receiving a second external signal; and
   reactivating the electronic circuit by increasing the cuff pressure until the sensor signal crosses the bistable threshold signal.

12. A method according to claim 11, wherein the external signals are transmitted by infrared transmission.

13. A method according to claim 11, wherein the external signals are transmitted by induction.

14. A method according to claim 11, wherein the external signals are transmitted by radio signals.

15. A method according to claim 1, further comprising the step of:
   Energizing the artificial fine-sensory sphincter implant by induction with an external device.

16. An apparatus for the electronic control of an artificial fine-sensory sphincter implant comprising:
   a cuff having a cuff pressure for closing the sphincter of a bladder;
   a sensor for sensing the differential between the internal bladder pressure and the cuff pressure;
   a comparator for comparing the differential pressure signal with a threshold value; and
   an actuator for controlling the cuff, so as to maintain the differential pressure between the cuff pressure and the internal bladder pressure within an upper threshold value and a lower threshold value, and wherein the cuff pressure may be selectively and temporarily increased above the upper threshold value in response to increases in the internal bladder pressure.

17. An apparatus according to claim 16, further comprising:
   (a) a differentiator element whose output signal of the differentiation is equivalent to the curve of the sensor signal;
   (b) an adding element with a monostable offset signal whose output signal is equivalent to the output signal of the differentiator element, increased by the monostable offset signal;
   (c) an integrator element that produces a monostable reference signal and a constant starting value, wherein selectively
      (i) the monostable reference signal is not equal to the monostable offset signal of the adding element and is selected such that the output signal of the adding element upon activity crosses the monostable reference signal, with the integrator element continuously or numerically integrating the difference between the output signal of the adding element and the monostable reference signal such that, upon low activity of the output signal of the differentiator element, the output signal of the integrator element will move away from the starting value, and upon high activity of the output signal of the differentiator element, will move towards the starting value, or
      (ii) the monostable reference signal is not equal to the output signal of the differentiator element upon low activity and is selected such that the output signal of the differentiator element, upon activity, crosses the monostable reference signal with the integrator element numerically integrating the difference between the output signal of the differentiator element and the monostable reference signal such that, upon low activity of the output signal of the differentiator element, the output signal of the integrator element will continuously move away from the starting value and, upon high activity of the output signal of the differentiator element, will move towards the starting value;
   (d) a comparator element with a bistable threshold signal whereby, in the event the sensor signal crosses the bistable threshold signal, the bistable threshold signal is changed by an amount due to hysteresis and the actuator decreases the cuff pressure until the sensor signal again crosses the bistable threshold signal, and whereby the actuator terminates the decrease of the cuff pressure and changes the bistable threshold signal by an amount due to hysteresis; and
   (e) a comparator element with a monostable threshold signal whereby, in the event the senor signal crosses the monostable threshold signal, the actuator terminates the increase of the cuff pressure and activates the integrator element, such that the output signal of the integrator element is equivalent to the constant starting value.

18. An apparatus according to claim 17, wherein the sensor signal is compared with the output signal of the adding element such that, in the event the sensor signal crosses the output signal of the adding element, the actuator increases the cuff pressure and deactivates the comparator element having a bistable threshold signal.

19. An apparatus according to claim 17, wherein in the event the output signal of the integrator element crosses with the monostable threshold signal, the actuator decreases the cuff pressure and activates the comparator element having a bistable threshold signal.

20. An apparatus according to claim 17, further comprising, a delaying element, which is activated upon triggering a pressure compensation between a pressure reservoir and the cuff by the comparator element, and upon reaching the set delay period, the actuator terminates the pressure compensation between the pressure reservoir and the cuff, and activates the integrator element, such that the output signal is in accordance with the constant starting value of the integrator element.

21. An apparatus according to claim 17, wherein the monostable offset signal may be varied by a parameter variation initiated by an external device.

22. An apparatus according to claim 17, wherein the bistable threshold signal may be varied by a parameter variation initiated by an external device.

23. An apparatus according to claim 17, wherein the monostable reference signal may be varied by a parameter variation initiated by an external device.

24. An apparatus according to claim 17, wherein the monostable threshold signal may be varied by a parameter variation initiated by an external device.

25. An apparatus according to claim 21, wherein the parameter variation is performed by the external device via infrared transmission.

26. An apparatus for miction control of the electronic circuit according to claim 16 wherein the actuator responds to a first external signal by decreasing the cuff pressure and the electronic circuit responds to the first external signal by deactivating the electronic circuit except for the comparator element with a bistable threshold signal; and wherein the actuator responds to a second external signal by increasing the cuff pressure until the sensor signal crosses the bistable threshold signal, thereby activating the electronic circuit.

27. An apparatus according to claim 26, wherein the first and second external signals are transmitted via infrared transmission.

28. An apparatus according to claim 26, wherein the first and second external signals are transmitted via radio.

29. An apparatus according to claim 26, wherein the first and second external signals are transmitted via induction.

30. An apparatus according to claim 16, further comprising a powering element, wherein the artificial fine-sensory sphincter implant may be energized by induction with an external device.

* * * * *